United States Patent
Dixon et al.

(10) Patent No.: US 7,749,976 B2
(45) Date of Patent: Jul. 6, 2010

(54) ISOLATED PTPMT1 PROTEIN WHICH MEDIATES INSULIN PRODUCTION AND USES THEREOF

(75) Inventors: Jack E. Dixon, San Diego, CA (US); David J. Pagliarini, Sommerville, MA (US)

(73) Assignee: The Regents of the University of California, Oakland, CA (US)

( * ) Notice: Subject to any disclaimer, the term of this patent is extended or adjusted under 35 U.S.C. 154(b) by 584 days.

(21) Appl. No.: 11/440,719

(22) Filed: May 24, 2006

(65) Prior Publication Data

US 2006/0292146 A1 Dec. 28, 2006

Related U.S. Application Data

(60) Provisional application No. 60/684,306, filed on May 24, 2005.

(51) Int. Cl.
*A01N 43/04* (2006.01)
*A61K 31/70* (2006.01)

(52) U.S. Cl. .................................................. 514/44
(58) Field of Classification Search .................... 514/44
See application file for complete search history.

(56) References Cited

OTHER PUBLICATIONS

Harborth et al. (2001) J. Cell Science 114:4557-4565.*
Holen et al. (2002) Nucleic Acids Res. 30:1757-1766.*
Boese et al., "Mechanical Insights Aid Computational Short Interfering RNA Design," Methods in Enzymology 392:73-96, 2005.*
Reynolds et al., "Rational siRNA design for RNA interference," Nature Biotechnology 22:326-330, 2004.*
Boisclair et al. Molecular Cell 19:291-2, 2005.*

* cited by examiner

*Primary Examiner*—Brian Whiteman
(74) *Attorney, Agent, or Firm*—Mandel & Adriano

(57) ABSTRACT

The invention identifies a novel protein tyrosine phosphatase, PTPMT1. The complete nucleic acid and amino acid sequence encoding PTPMT1 is provided. Methods are provided for preventing and/or treating type II diabetes by regulating PTPMT1 levels, which in turn regulates insulin levels.

6 Claims, 21 Drawing Sheets

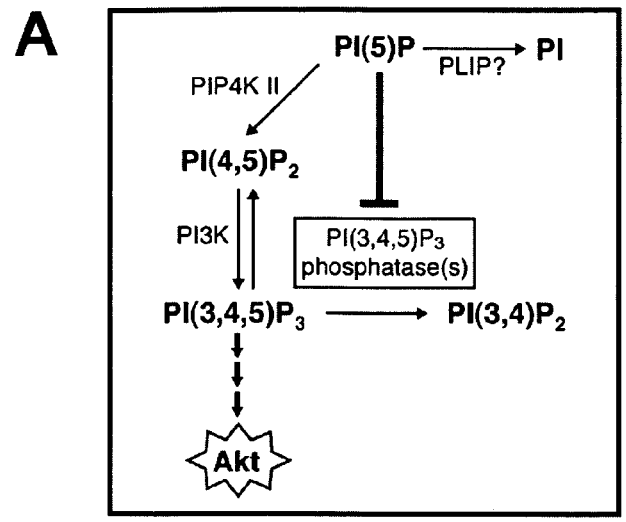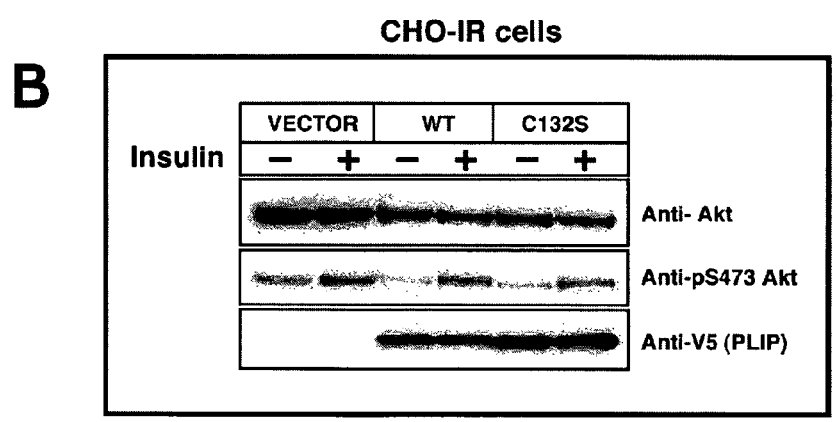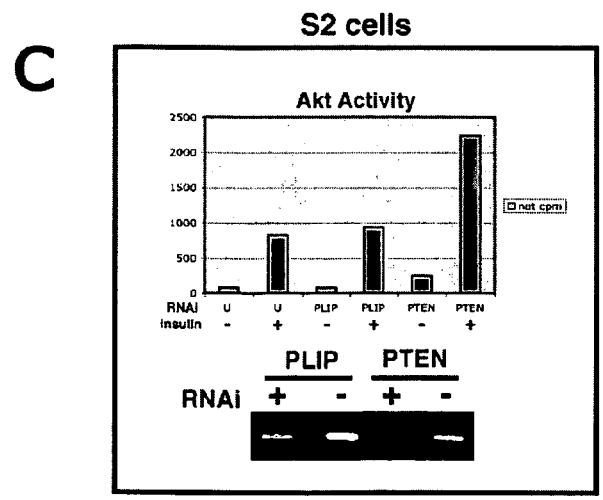
Figure 5 sense: 5'-GUCUGUGGAUGACAAAGAAtt-3'
antisense:UUCUUUGUCAUCCACAGACtt-3

Figure 13 sense strand: 5' gccaguuggaaauucucaatt 3'
antisense strand: 5' uugagaauuuccaacuggctg 3'

Figure 14 sense strand: 5' guuggaaauucucaaagagtt 3'
antisense strand: 5' cucuuugagaauuuccaactg 3'

Figure 15

```
ATGGCAGCATCCGCGTGGCTGGAGGCCGGCCTGGCCCGGGTGCTCTTCTA
CCCGACGCTGCTCTACACAGTGTTCCGGGGGAGGGTGCGCGGCCCGGCG
CACCGCGACTGGTACCACCGCATCGACCACACGGTTCTGCTGGGCGCGCT
GCCGCTGAAGAACATGACGCGCCGGCTGGTACTGGACGAGAACGTGCGCG
GGGTGATCACTATGAACGAGGAGTACGAGACCCGATTCCTGTGCAACACCT
CGAAGGAATGGAAGAAAGCAGGAGTTGAGCAGCTACGGCTCAGCACAGTC
GACATGACTGGGGTCCCAACCTTGGCCAATCTCCACAAAGGAGTCCAGTTT
GCTCTCAAGTACCAGGCACTGGGCCAGTGTGTCTATGTGCATTGTAAGGCT
GGTCGATCCAGAAGTGCCACAATGGTGGCAGCCTATCTGATTCAGGTACAC
AACTGGAGCCCAGAGGAGGCTATAGAAGCGATCGCCAAAATCCGGTCACA
CATCTCCATCAGGCCCAGCCAGCTGGAAGTTCTCAAAGAGTTCCACAAGGA
GATCACTGCAAGGGCAGCAAAGAATTAA
```

Figure 16

MAASAWLEAGLARVLFYPTLLYTVFRGRVRGPAHRDWYHRIDHTVLLGALPLK
NMTRRLVLDENVRGVITMNEEYETRFLCNTSKEWKKAGVEQLRLSTVDMTGVP
TLANLHKGVQFALKYQALGQCVYVHCKAGRSRSATMVAAYLIQVHNWSPEEAI
EAIAKIRSHISIRPSQLEVLKEFHKEITARAAKN

Figure 17

```
ATGGCTCCTGTTCCGGGATCCCTCGGGCAGGGCCGGGACTCCGGGGACTC
AGCTTCGAAGAGTCGGGAGGCATCAGGTGGCCCTCAGCTCTCGTCCTCCG
CGTCCTTCTCGCGGTGGCTGGTCGCGAGCCCCGGGGCCGGTGGCTGGCC
GCTGCGCCTGGCGGGGTGGGGCGCCTCGCCACTGCGCCTGGCGGGGTGG
GGCGGGATGGCGGCCTCCGCGTGGCTGGAGGCCGGCCTGGCCCGGGTGC
TCTTCTACCCGACGCTGCTCTACACAGTGTTCCGGGGGAGGGTGCGCGGC
CCGGCGCACCGCGACTGGTACCACCGCATCGACCACACGGTTCTGCTGGG
CGCGCTGCCGCTGAAGAACATGACGCGCCGGCTGGTACTGGACGAGAACG
TGCGCGGGGTGATCACTATGAACGAGGAGTACGAGACCCGATTCCTGTGC
AACACCTCGAAGGAATGGAAGAAAGCAGGAGTTGAGCAGCTACGGCTCAG
CACAGTCGACATGACTGGGGTCCCAACCTTGGCCAATCTCCACAAAGGAGT
CCAGTTTGCTCTCAAGTACCAGGCACTGGGCCAGTGTGTCTATGTGCATTG
TAAGGCTGGTCGATCCAGAAGTGCCACAATGGTGGCAGCCTATCTGATTCA
GGTACACAACTGGAGCCCAGAGGAGGCTATAGAAGCGATCGCCAAAATCC
GGTCACACATCTCCATCAGGCCCAGCCAGCTGGAAGTTCTCAAAGAGTTCC
ACAAGGAGATCACTGCAAGGGCAGCAAAGAATTAA
```

Figure 18

SEQUENCE LISTING

<160> NUMBER OF SEQ ID NOS: 49

<210> SEQ ID NO 1
<211> LENGTH: 7
<212> TYPE: PRT
<213> ORGANISM: Mus musculus

<400> SEQUENCE: 1

-continued

```
Cys Lys Ala Gly Lys Gly Arg
1               5
```

<210> SEQ ID NO 2
<211> LENGTH: 7
<212> TYPE: PRT
<213> ORGANISM: Artificial
<220> FEATURE:
<223> OTHER INFORMATION: P-loop catalytic motif
<220> FEATURE:
<221> NAME/KEY: misc_feature
<222> LOCATION: (2)..(6)
<223> OTHER INFORMATION: Xaa can be any naturally occurring amino acid

<400> SEQUENCE: 2

```
Cys Xaa Xaa Xaa Xaa Xaa Arg
1               5
```

<210> SEQ ID NO 3
<211> LENGTH: 21
<212> TYPE: DNA
<213> ORGANISM: Artificial
<220> FEATURE:
<223> OTHER INFORMATION: Designed to be complementary to mouse sequences

<400> SEQUENCE: 3 gucguggau gacaaagaat t                                              21

<210> SEQ ID NO 4
<211> LENGTH: 21
<212> TYPE: DNA
<213> ORGANISM: Artificial
<220> FEATURE:
<223> OTHER INFORMATION: Designed to be complementary to mouse sequences

<400> SEQUENCE: 4
uucuuuguca uccacagact t                                             21

<210> SEQ ID NO 5
<211> LENGTH: 21
<212> TYPE: DNA
<213> ORGANISM: Artificial
<220> FEATURE:
<223> OTHER INFORMATION: Designed to be complementary to mouse sequences

<400> SEQUENCE: 5
gccaguugga aauucucaat t                                             21

<210> SEQ ID NO 6
<211> LENGTH: 21
<212> TYPE: DNA
<213> ORGANISM: Artificial
<220> FEATURE:
<223> OTHER INFORMATION: Designed to be complementary to mouse sequences

<400> SEQUENCE: 6
uugagaauuu ccaacuggct g                                             21

<210> SEQ ID NO 7
<211> LENGTH: 21
<212> TYPE: DNA
<213> ORGANISM: Artificial
<220> FEATURE:
<223> OTHER INFORMATION: Designed to be complementary to mouse sequences

<400> SEQUENCE: 7
guuggaaauu cucaaagagt t                                             21

<210> SEQ ID NO 8
<211> LENGTH: 21
<212> TYPE: DNA
<213> ORGANISM: Artificial
<220> FEATURE:
<223> OTHER INFORMATION: Designed to be complementary to mouse sequences

<400> SEQUENCE: 8
cucuuugaga auuuccaact g                                             21

<210> SEQ ID NO 9
<211> LENGTH: 26
<212> TYPE: DNA
<213> ORGANISM: Artificial
<220> FEATURE:
<223> OTHER INFORMATION: PLIP forward primer

<400> SEQUENCE: 9
ccaccgcatc gaccacacgg ttctgc                                        26

<210> SEQ ID NO 10
<211> LENGTH: 34
<212> TYPE: DNA
<213> ORGANISM: Artificial
<220> FEATURE:
<223> OTHER INFORMATION: PLIP reverse primer

<400> SEQUENCE: 10
cctcctctgg gctccagttg tgtacctgaa tcag                               34

<210> SEQ ID NO 11
<211> LENGTH: 7
<212> TYPE: PRT
<213> ORGANISM: Mus musculus

<400> SEQUENCE: 11

Cys Lys Ala Gly Arg Ser Arg
1               5

<210> SEQ ID NO 12
<211> LENGTH: 18
<212> TYPE: PRT
<213> ORGANISM: Mus musculus

<400> SEQUENCE: 12

Val Tyr Val His Cys Lys Ala Gly Arg Ser Arg Ser Ala Thr Met Val
1               5                   10                  15

Ala Ala

<210> SEQ ID NO 13
<211> LENGTH: 18
<212> TYPE: PRT
<213> ORGANISM: Mus musculus

<400> SEQUENCE: 13

Ala Ala Ile His Cys Lys Ala Gly Lys Gly Arg Thr Gly Val Met Ile
1               5                   10                  15

Cys Ala

<210> SEQ ID NO 14
<211> LENGTH: 18
<212> TYPE: PRT
<213> ORGANISM: Mus musculus

<400> SEQUENCE: 14

```
Val Ala Ile His Cys Lys Gly Gly Lys Gly Arg Thr Gly Thr Met Val
1               5                   10                  15

Cys Ala

<210> SEQ ID NO 15
<211> LENGTH: 18
<212> TYPE: PRT
<213> ORGANISM: Mus musculus

<400> SEQUENCE: 15

Val Ala Ile His Cys Lys Gly Gly Lys Gly Arg Thr Gly Thr Met Val
1               5                   10                  15

Cys Ala

<210> SEQ ID NO 16
<211> LENGTH: 18
<212> TYPE: PRT
<213> ORGANISM: Salmonella typhimurium

<400> SEQUENCE: 16

Pro Ala Trp Asn Cys Lys Ser Gly Lys Asp Arg Thr Gly Met Met Asp
1               5                   10                  15

Ser Glu

<210> SEQ ID NO 17
<211> LENGTH: 18
<212> TYPE: PRT
<213> ORGANISM: Escherichia coli

<400> SEQUENCE: 17

Pro Cys Trp Asn Cys Lys Ser Gly Lys Asp Arg Thr Gly Met Gln Asp
1               5                   10                  15

Ala Glu

<210> SEQ ID NO 18
<211> LENGTH: 18
<212> TYPE: PRT
<213> ORGANISM: Mus musculus

<400> SEQUENCE: 18

Arg Phe Thr Ser Cys Lys Ser Ala Lys Asp Arg Thr Ala Met Ser Val
1               5                   10                  15

Thr Leu

<210> SEQ ID NO 19
<211> LENGTH: 18
<212> TYPE: PRT
<213> ORGANISM: Mus musculus

<400> SEQUENCE: 19

Arg Phe Thr Cys Cys Lys Ser Ala Lys Asp Arg Thr Ser Met Ser Val
1               5                   10                  15

Thr Leu

<210> SEQ ID NO 20
<211> LENGTH: 21
<212> TYPE: PRT
<213> ORGANISM: Homo sapiens

<400> SEQUENCE: 20

Val Tyr Val His Cys Lys Ala Gly Arg Ser Arg Ser Ala Thr Met Val
```

```
                1               5                  10                  15

Ala Ala Tyr Leu Ile
            20

<210> SEQ ID NO 21
<211> LENGTH: 21
<212> TYPE: PRT
<213> ORGANISM: Mus musculus

<400> SEQUENCE: 21

Val Tyr Val His Cys Lys Ala Gly Arg Ser Arg Ser Ala Thr Met Val
1               5                  10                  15

Ala Ala Tyr Leu Ile
            20

<210> SEQ ID NO 22
<211> LENGTH: 21
<212> TYPE: PRT
<213> ORGANISM: Gallus gallus

<400> SEQUENCE: 22

Val Tyr Val His Cys Lys Ala Gly Arg Ser Arg Ser Ala Thr Val Val
1               5                  10                  15

Ala Ala Tyr Leu Ile
            20

<210> SEQ ID NO 23
<211> LENGTH: 21
<212> TYPE: PRT
<213> ORGANISM: Takifugu rubripes

<400> SEQUENCE: 23

Val Tyr Ile His Cys Lys Ala Gly Arg Ser Arg Ser Ala Thr Leu Val
1               5                  10                  15

Ala Ala Tyr Leu Ile
            20

<210> SEQ ID NO 24
<211> LENGTH: 21
<212> TYPE: PRT
<213> ORGANISM: Danio rerio

<400> SEQUENCE: 24

Val Tyr Ile His Cys Lys Ala Gly Arg Ser Arg Ser Ala Thr Ile Ala
1               5                  10                  15

Ala Ala Tyr Leu Ile
            20

<210> SEQ ID NO 25
<211> LENGTH: 21
<212> TYPE: PRT
<213> ORGANISM: Ciona intestinalis

<400> SEQUENCE: 25

Val Tyr Val His Cys Lys Ala Gly Arg Thr Arg Ser Ala Thr Val Ala
1               5                  10                  15

Val Cys Tyr Leu Met
            20

<210> SEQ ID NO 26
<211> LENGTH: 21
<212> TYPE: PRT
<213> ORGANISM: Drosophila melanogaster
```

<400> SEQUENCE: 26

Val Tyr Val His Cys Lys Ala Gly Arg Thr Arg Ser Ala Thr Leu Val
1               5                   10                  15

Gly Cys Tyr Leu Met
            20

<210> SEQ ID NO 27
<211> LENGTH: 21
<212> TYPE: PRT
<213> ORGANISM: Anopheles gambiae

<400> SEQUENCE: 27

Ile Tyr Val His Cys Lys Ala Gly Arg Thr Arg Ser Ala Thr Leu Val
1               5                   10                  15

Gly Cys Tyr Leu Ile
            20

<210> SEQ ID NO 28
<211> LENGTH: 21
<212> TYPE: PRT
<213> ORGANISM: Caenorhabditis elegans

<400> SEQUENCE: 28

Val Tyr Val His Cys Lys Ala Gly Arg Thr Arg Ser Ala Thr Val Ala
1               5                   10                  15

Thr Cys Tyr Leu Met
            20

<210> SEQ ID NO 29
<211> LENGTH: 21
<212> TYPE: PRT
<213> ORGANISM: Caenorhabditis briggsae

<400> SEQUENCE: 29

Val Tyr Val His Cys Lys Ala Gly Arg Thr Arg Ser Ala Thr Val Ala
1               5                   10                  15

Thr Cys Tyr Leu Met
            20

<210> SEQ ID NO 30
<211> LENGTH: 21
<212> TYPE: PRT
<213> ORGANISM: Echinococcus granulosus

<400> SEQUENCE: 30

Val Tyr Ile His Cys Lys Ala Gly Arg Thr Arg Ser Ala Phe Ile Val
1               5                   10                  15

Thr Cys Tyr Phe Met
            20

<210> SEQ ID NO 31
<211> LENGTH: 21
<212> TYPE: PRT
<213> ORGANISM: Hydra magnipapillata

<400> SEQUENCE: 31

Val Tyr Val His Cys Lys Ala Ser Arg Ser Arg Ser Ala Thr Val Val
1               5                   10                  15

Val Cys Tyr Leu Ile
            20

```
<210> SEQ ID NO 32
<211> LENGTH: 21
<212> TYPE: PRT
<213> ORGANISM: Lycopersicon esculentum

<400> SEQUENCE: 32

Thr Tyr Val His Cys Lys Ala Gly Arg Gly Arg Ser Thr Thr Ile Val
1               5                   10                  15

Leu Cys Tyr Leu Val
            20

<210> SEQ ID NO 33
<211> LENGTH: 21
<212> TYPE: PRT
<213> ORGANISM: Arabidopsis thaliana

<400> SEQUENCE: 33

Thr Tyr Val His Cys Lys Ala Gly Arg Gly Arg Ser Thr Thr Val Val
1               5                   10                  15

Leu Cys Tyr Leu Ile
            20

<210> SEQ ID NO 34
<211> LENGTH: 21
<212> TYPE: PRT
<213> ORGANISM: Oryza sativa

<400> SEQUENCE: 34

Thr Tyr Val His Cys Lys Ala Gly Arg Gly Arg Ser Thr Thr Ile Val
1               5                   10                  15

Leu Cys Tyr Leu Ile
            20

<210> SEQ ID NO 35
<211> LENGTH: 21
<212> TYPE: PRT
<213> ORGANISM: Zea mays

<400> SEQUENCE: 35

Thr Tyr Val His Cys Lys Ala Gly Arg Gly Arg Ser Thr Thr Val Val
1               5                   10                  15

Ile Cys Tyr Leu Val
            20

<210> SEQ ID NO 36
<211> LENGTH: 21
<212> TYPE: PRT
<213> ORGANISM: Pinus taeda

<400> SEQUENCE: 36

Thr Tyr Val His Cys Lys Ala Gly Arg Gly Arg Ser Thr Thr Ile Val
1               5                   10                  15

Leu Cys Tyr Leu Val
            20

<210> SEQ ID NO 37
<211> LENGTH: 21
<212> TYPE: PRT
<213> ORGANISM: Dictyostelium discoideum

<400> SEQUENCE: 37

Val Tyr Ile His Cys Lys Ala Gly Arg Gly Arg Ser Gly Ala Ile Ala
1               5                   10                  15
```

```
Ile Cys Trp Ile Ala
            20

<210> SEQ ID NO 38
<211> LENGTH: 21
<212> TYPE: PRT
<213> ORGANISM: Pirellula sp.

<400> SEQUENCE: 38

Val Tyr Ile His Cys Lys Ala Gly Arg Ala Arg Ser Ala Thr Ile Ala
1               5                   10                  15

Ile Cys Trp Leu Ile
            20

<210> SEQ ID NO 39
<211> LENGTH: 261
<212> TYPE: PRT
<213> ORGANISM: Mus musculus

<400> SEQUENCE: 39

Met Ala Pro Val Pro Gly Ser Leu Gly Gln Gly Arg Asp Ser Gly Asp
1               5                   10                  15

Ser Ala Ser Lys Ser Arg Glu Ala Gly Gly Pro Gln Leu Ser Ser
                20                  25                  30

Ser Ala Ser Phe Ser Arg Trp Leu Val Ala Ser Pro Gly Ala Gly Gly
            35                  40                  45

Trp Pro Leu Arg Leu Ala Gly Trp Gly Ala Ser Pro Leu Arg Leu Ala
        50                  55                  60

Gly Trp Gly Gly Met Ala Ala Ser Ala Trp Leu Glu Ala Gly Leu Ala
65                  70                  75                  80

Arg Val Leu Phe Tyr Pro Thr Leu Leu Tyr Thr Val Phe Arg Gly Arg
                85                  90                  95

Val Arg Gly Pro Ala His Arg Asp Trp Tyr His Arg Ile Asp His Thr
            100                 105                 110

Val Leu Leu Gly Ala Leu Pro Leu Lys Asn Met Thr Arg Arg Leu Val
        115                 120                 125

Leu Asp Glu Asn Val Arg Gly Val Ile Thr Met Asn Glu Glu Tyr Glu
    130                 135                 140

Thr Arg Phe Leu Cys Asn Thr Ser Lys Glu Trp Lys Lys Ala Gly Val
145                 150                 155                 160

Glu Gln Leu Arg Leu Ser Thr Val Asp Met Thr Gly Val Pro Thr Leu
                165                 170                 175

Ala Asn Leu His Lys Gly Val Gln Phe Ala Leu Lys Tyr Gln Ala Leu
            180                 185                 190

Gly Gln Cys Val Tyr Val His Cys Lys Ala Gly Arg Ser Arg Ser Ala
        195                 200                 205

Thr Met Val Ala Ala Tyr Leu Ile Gln Val His Asn Trp Ser Pro Glu
    210                 215                 220

Glu Ala Ile Glu Ala Ile Ala Lys Ile Arg Ser His Ile Ser Ile Arg
225                 230                 235                 240

Pro Ser Gln Leu Glu Val Leu Lys Glu Phe His Lys Glu Ile Thr Ala
                245                 250                 255

Arg Ala Ala Lys Asn
            260

<210> SEQ ID NO 40
<211> LENGTH: 193
<212> TYPE: PRT
```

<213> ORGANISM: Mus musculus

<400> SEQUENCE: 40

Met Ala Ser Ala Trp Leu Glu Ala Gly Leu Ala Arg Val Leu Phe
1               5                   10                  15

Tyr Pro Thr Leu Leu Tyr Thr Val Phe Arg Gly Arg Val Arg Gly Pro
            20                  25                  30

Ala His Arg Asp Trp Tyr His Arg Ile Asp His Thr Val Leu Leu Gly
        35                  40                  45

Ala Leu Pro Leu Lys Asn Met Thr Arg Arg Leu Val Leu Asp Glu Asn
    50                  55                  60

Val Arg Gly Val Ile Thr Met Asn Glu Glu Tyr Glu Thr Arg Phe Leu
65                  70                  75                  80

Cys Asn Thr Ser Lys Glu Trp Lys Lys Ala Gly Val Glu Gln Leu Arg
                85                  90                  95

Leu Ser Thr Val Asp Met Thr Gly Val Pro Thr Leu Ala Asn Leu His
            100                 105                 110

Lys Gly Val Gln Phe Ala Leu Lys Tyr Gln Ala Leu Gly Gln Cys Val
        115                 120                 125

Tyr Val His Cys Lys Ala Gly Arg Ser Arg Ser Ala Thr Met Val Ala
    130                 135                 140

Ala Tyr Leu Ile Gln Val His Asn Trp Ser Pro Glu Glu Ala Ile Glu
145                 150                 155                 160

Ala Ile Ala Lys Ile Arg Ser His Ile Ser Ile Arg Pro Ser Gln Leu
                165                 170                 175

Glu Val Leu Lys Glu Phe His Lys Glu Ile Thr Ala Arg Ala Ala Lys
            180                 185                 190

Asn

<210> SEQ ID NO 41
<211> LENGTH: 14
<212> TYPE: PRT
<213> ORGANISM: Pirellula sp.

<400> SEQUENCE: 41

Met Ser Gly Pro Ile Gln Ser Gly Trp Leu Arg Arg Leu Tyr
1               5                   10

<210> SEQ ID NO 42
<211> LENGTH: 83
<212> TYPE: DNA
<213> ORGANISM: Pirellula sp.

<400> SEQUENCE: 42
gaagccgctt tggccatcga cgatcgagcg atccacacgg catgagcggt cccatccagt    60
ccggttggct gaggcgattg tac                                            83

<210> SEQ ID NO 43
<211> LENGTH: 14
<212> TYPE: PRT
<213> ORGANISM: Pirellula sp.

<400> SEQUENCE: 43

Glu Ala Ala Leu Ala Ile Asp Asp Arg Ala Ile His Thr Ala
1               5                   10

<210> SEQ ID NO 44
<211> LENGTH: 582
<212> TYPE: DNA

<213> ORGANISM: Mus musculus

<400> SEQUENCE: 44

```
atggcagcat ccgcgtggct ggaggccggc ctggcccggg tgctcttcta cccgacgctg      60
ctctacacag tgttccgggg gagggtgcgc ggcccggcgc accgcgactg gtaccaccgc     120
atcgaccaca cggttctgct gggcgcgctg ccgctgaaga acatgacgcg ccggctggta     180
ctggacgaga acgtgcgcgg ggtgatcact atgaacgagg agtacgagac ccgattcctg     240
tgcaacacct cgaaggaatg aagaaagca ggagttgagc agctacggct cagcacagtc     300
gacatgactg ggtcccaac cttggccaat ctccacaaag gagtccagtt tgctctcaag     360
taccaggcac tgggccagtg tgtctatgtg cattgtaagg ctggtcgatc cagaagtgcc     420
acaatggtgg cagcctatct gattcaggta cacaactgga gcccagagga ggctatagaa     480
gcgatcgcca aaatccggtc acacatctcc atcaggccca gccagctgga agttctcaaa     540
gagttccaca aggagatcac tgcaagggca gcaaagaatt aa                        582
```

<210> SEQ ID NO 45
<211> LENGTH: 786
<212> TYPE: DNA
<213> ORGANISM: Mus musculus

<400> SEQUENCE: 45

```
atggctcctg ttccgggatc cctcgggcag ggccgggact ccggggactc agcttcgaag      60
agtcggagg catcaggtgg ccctcagctc tcgtcctccg cgtccttctc gcggtggctg     120
gtcgcgagcc ccggggccgg tggctggccg ctgcgcctgg cggggtgggg cgcctcgcca     180
ctgcgcctgg cggggtgggg cgggatggcg gcctccgcgt ggctggaggc cggcctggcc     240
cgggtgctct tctacccgac gctgctctac acagtgttcc gggggagggt gcgcggcccg     300
gcgcaccgcg actggtacca ccgcatcgac cacgggttc tgctgggcgc gctgccgctg     360
aagaacatga cgcgccggct ggtactggac gagaacgtgc gcggggtgat cactatgaac     420
gaggagtacg agacccgatt cctgtgcaac acctcgaagg aatggaagaa agcaggagtt     480
gagcagctac ggctcagcac agtcgacatg actggggtcc caaccttggc caatctccac     540
aaaggagtcc agtttgctct caagtaccag gcactgggcc agtgtgtcta tgtgcattgt     600
aaggctggtc gatccagaag tgccacaatg gtggcagcct atctgattca ggtacacaac     660
tggagcccag aggaggctat agaagcgatc gccaaaatcc ggtcacacat ctccatcagg     720
cccagccagc tggaagttct caagagttc cacaaggaga tcactgcaag ggcagcaaag     780
aattaa                                                               786
```

<210> SEQ ID NO 46
<211> LENGTH: 174
<212> TYPE: PRT
<213> ORGANISM: Mus musculus

<400> SEQUENCE: 46

```
Leu Leu Tyr Thr Val Phe Arg Gly Arg Val Arg Gly Pro Ala His Arg
 1               5                  10                  15

Asp Trp Tyr His Arg Ile Asp His Thr Val Leu Leu Gly Ala Leu Pro
             20                  25                  30

Leu Lys Asn Met Thr Arg Arg Leu Val Leu Asp Glu Asn Val Arg Gly
         35                  40                  45

Val Ile Thr Met Asn Glu Glu Tyr Glu Thr Arg Phe Leu Cys Asn Thr
     50                  55                  60
```

```
Ser Lys Glu Trp Lys Lys Ala Gly Val Glu Gln Leu Arg Leu Ser Thr
 65                  70                  75                  80

Val Asp Met Thr Gly Val Pro Thr Leu Ala Asn Leu His Lys Gly Val
                 85                  90                  95

Gln Phe Ala Leu Lys Tyr Gln Ala Leu Gly Gln Cys Val Tyr Val His
            100                 105                 110

Cys Lys Ala Gly Arg Ser Arg Ser Ala Thr Met Val Ala Ala Tyr Leu
            115                 120                 125

Ile Gln Val His Asn Trp Ser Pro Glu Glu Ala Ile Glu Ala Ile Ala
        130                 135                 140

Lys Ile Arg Ser His Ile Ser Ile Arg Pro Ser Gln Leu Glu Val Leu
145                 150                 155                 160

Lys Glu Phe His Lys Glu Ile Thr Ala Arg Ala Ala Lys Asn
                165                 170
```

<210> SEQ ID NO 47
<211> LENGTH: 525
<212> TYPE: DNA
<213> ORGANISM: Mus musculus

<400> SEQUENCE: 47

```
ctgctctaca cagtgttccg ggggagggtg cgcggcccgg cgcaccgcga ctggtaccac      60
cgcatcgacc acacggttct gctgggcgcg ctgccgctga gaacatgac gcgccggctg      120
gtactggacg agaacgtgcg cggggtgatc actatgaacg aggagtacga gacccgattc     180
ctgtgcaaca cctcgaagga atggaagaaa gcagagttg agcagctacg gctcagcaca      240
gtcgacatga ctggggtccc aaccttggcc aatctccaca aggagtccca gtttgctctc     300
aagtaccagg cactgggcca gtgtgtctat gtgcattgta aggctggtcg atccagaagt     360
gccacaatgg tggcagccta tctgattcag gtacacaact ggagcccaga ggaggctata     420
gaagcgatcg ccaaaatccg gtcacacatc tccatcaggc ccagccagct ggaagttctc     480
aaagagttcc acaaggagat cactgcaagg gcagcaaaga attaa                    525
```

<210> SEQ ID NO 48
<211> LENGTH: 19
<212> TYPE: PRT
<213> ORGANISM: Mus musculus

<400> SEQUENCE: 48

```
Ile His Cys Lys Ala Gly Lys Gly Arg Thr Gly Val Met Ile Cys Ala
1                5                  10                  15

Tyr Leu Leu
```

<210> SEQ ID NO 49
<211> LENGTH: 19
<212> TYPE: PRT
<213> ORGANISM: Mus musculus

<400> SEQUENCE: 49

```
Val His Cys Lys Ala Gly Lys Ser Arg Ser Ala Thr Met Val Ala Ala
1                5                  10                  15

Tyr Leu Ile
```

ISOLATED PTPMT1 PROTEIN WHICH MEDIATES INSULIN PRODUCTION AND USES THEREOF

This application claims priority to provisional patent application, U.S. Ser. No. 60/684,306, filed May 24, 2005, the contents of which are hereby incorporated by reference in their entirety herein.

Throughout this application various publications are referenced. The disclosures of these publications in their entireties are hereby incorporated by reference into this application in order to more fully describe the state of the art to which this invention pertains.

This invention was made with government support under NIH Grant Nos. DK18849-31, 18024, and NIH 2 T32 GM07752-25 (D.J.P.). The government has certain rights in the invention.

FIELD OF THE INVENTION

The present invention relates to identification, localization and characterization of PTPMT1 proteins and defines PTPMT1 as potential new drug targets for the treatment of PTPMT1 associated diseases, e.g., type II diabetes. The invention also provides methods for increasing insulin production, thereby treating or preventing type II diabetes.

BACKGROUND OF THE INVENTION

The past two or three decades have established a seminal role for Protein Tyrosine Phosphatases (PTPs) in human health and disease (Alonso et al., 2004; Andersen et al., 2004). Gene mutations in members of this family result in metabolic, neurological, muscle wasting, and autoimmune diseases, and over 30 have been implicated in the etiology of various cancers (Alonso et al., 2004).

PTPs are a family of approximately 100 phosphatases characterized by their highly conserved $CX_5R$ (SEQ ID NO:2) catalytic motif. Once thought to dephosphorylate only phosphotyrosine residues, a subset of PTP's are now known to dephosphorylate phosphoserine- and phosphothreonine-containing proteins, as well as to use RNA, and phosphoinositides as substrates in vitro and in vivo (Tonks et. al., 2001; Li et al., 2000; Andersen et al., 2001; Fauman et al., 1996; Jackson et al., 2001). A structural study of the tumor suppressor phosphatase PTEN revealed a wider active site cleft and suggested positions of key basic amino acids in the P-loop (C<u>K</u>AG <u>K</u>GR) (SEQ ID NO:1) among the reasons for its ability to use the phosphoinositide $PI(3,4,5)P_3$ as its preferred substrate (Lee et al., 1999). Consistent with this observation, other PTP's possessing highly similar or identical active site motifs, including the PTEN homologs PTEN 2 and TPIP, bacterial effector phosphatases SopB and IpgD, and inositol polyphosphate 4 phosphatases 1 and 2, have also now been shown to possess activity against phosphoinositide substrates (Morris et al., 2000; Walker et al., 2001; Wu et al., 2001; Niebuhr et al., 2002; Norris et al., 1998; Bansal et al., 1990; Norris et al., 1994).

Phosphatidylinositol (PtdIns), an abundant membrane phospholipid, is capable of being phosphorylated on the 3, 4, and 5 positions of its inositol ring to form seven unique lipid signaling molecules collectively termed phosphoinositides (PI's) (Vanhaesebroeck et al., 2001). PI's regulate critical cellular functions, including apoptosis, membrane trafficking, cytoskeletal rearrangement, metabolism, growth, and differentiation, by altering the subcellular location, state of aggregation, and activity of a variety of cellular enzymes. PI regulation by lipid kinases, phosphatases, and lipases is therefore critical in achieving proper cellular responses to outside stress (Vanhaesebroeck et al., 2001; Wishart et al., 2002). PI(5)P (phosphatidylinositol-5 phosphate) is the least characterized PI, having only recently been identified as an endogenous lipid (Rameh et al., 1997). Recent studies report changes in intracellular PI(5)P levels during cell cycle progression, as well as upon thrombin treatment and osmotic stress (Morris et al., 2000; Clarke et al., 2001; Meijer et al., 2001). Furthermore, the PHD (plant homeodomain)-containing ING2 protein, a candidate tumor suppressor, was recently shown to act as a nuclear PI(5)P receptor a function that regulates its ability to activate p53 (Gozani et al., 2003). PI(5)P has also been tied to tumor suppression via its potential regulation of Akt. It was recently demonstrated that loss of PI(5)P, via conversion to $PI(4,5)P_2$ by the phosphoinositide kinase PIP4K II, resulted in a decrease in Akt activity (Carricaburu et al., 2003). Lastly, PI(5)P has been shown to enhance the activity of various myotubularin phosphatases (MTM1, MTMR3, and MTMR6) toward their preferred substrate $PI(3,5)P_2$, presumably through allosteric regulation (Schaletzky et al., 2003). Together these studies stress the importance of PI(5)P as a bona fide signaling molecule, and not merely a metabolic precursor to other PI's as once proposed.

Protein tyrosine phosphatase localized to the mitochondrion (PTPMT1) is a member of the PTP superfamily discussed above, characterized by their highly conserved $CX_5R$ (SEQ ID NO:2) catalytic motif. Mitochondria are ubiquitous and dynamic organelles that house many crucial cellular processes in eukaryotic organisms. In addition to being responsible for the production of over 90% of cellular ATP through the TCA cycle and oxidative phosphorylation, mitochondria are the site of fatty acid oxidation, ketone body production, heme biosynthesis, cardiolipin metabolism, the production of coenzyme Q, ROS production, key steps of gluconeogenesis and the urea cycle, and are central to the mechanisms of apoptosis (Newmeyer and Ferguson-Miller, 2003; Voet, 2004). More specialized mitochondrial functions, including the coupling of glucose metabolism to insulin secretion in the pancreatic β cell, have also evolved in various tissues (Maechler and Wollheim, 2001). Disruption of these and other mitochondrial functions results in more than 40 known diseases, including Parkinson's, Alzheimer's and diabetes, further underscoring the importance of properly functioning mitochondria to human health (UMDF, 2004; Pestronka, 2004; Schon, 2000; Wallace, 1999).

Despite the level of attention given to mitochondrial function during the past approximately 50 years, there remains only a vague understanding of the role of phosphorylation within this organelle. To date, the phosphorylation and dephosphorylation of the E1 subunits of the pyruvate and branched-chain α-ketoacid dehydrogenase complexes (PDC and BCKD) constitute the only well-characterized examples of regulation by reversible phosphorylation within mitochondria (Harris et al., 1997; Roche et al., 2001). However, a number of studies suggest that phosphorylation is more widely important in mitochondrial physiology. Multiple groups have reported that the addition of radiolabeled ATP to purified mitochondria leads to the formation of an array of phosphoproteins, the number of which increases with the addition of phosphatase inhibitors. The recent introduction of a novel phospho-specific dye, allowing for the observation of steady-state phosphorylation, has further contributed to the list of potential mitochondrial phosphoproteins (Schulenberg et al., 2003). Approximately 25 of these proteins have been identified, including respiratory chain subunits and multiple members of the TCA cycle (Bijur and Jope, 2003; Bykova et al., 2003; Chen et al., 2004; Hojlund et al., 2003; Lee et al., 2004; Schulenberg et al., 2003). The discovery of mitochondrial kinases and phosphatases capable of regulating these phosphoproteins is thus of critical importance in determining the functional consequences of these phosphorylation events.

As part of our discovery, it was realized that PTPMT1 is among the most highly conserved phosphatases known, possessing orthologs in all four phylogenetic kingdoms, including the eubacterium *Pirellula* sp. strain 1. Additionally, PTPMT1 is the first member of the PTP superfamily to reside exclusively within the mitochondrion. PTPMT1 is directed to the mitochondrion by a cryptic N-terminal signal sequence where it colocalizes with members of the respiratory chain on the matrix face of the inner membrane. Disruption of PTPMT1 expression in the pancreatic β cell line INS-1 832/13 causes an approximate 80% increase ATP production, and markedly enhances insulin secretion under both basal and glucose stimulated conditions. This same treatment alters the mitochondrial phosphoprotein profile, suggesting that these observed biological effects may be due to a phosphorylation event or events involving PTPMT1. Together, these data suggest a possible new mitochondrial control point in the regulation of insulin secretion from β cells, and define PTPMT1 as a possible new drug target for the treatment of type II diabetes. Moreover, the discovery of a bona fide mitochondrial PTP further suggests that crucial mitochondrial functions are likely to be regulated by reversible phosphorylation.

SUMMARY OF THE INVENTION

The present invention provides the complete and correct, isolated and purified DNA sequence encoding the amino acid sequence corresponding to PTPMT1. In one embodiment, the isolated PTPMT1 protein is encoded by 193 amino acids. In another embodiment, the isolated PTPMT1 protein is encoded by 174 amino acids.

The invention also provides a method for producing a PTPMT1 protein molecule. This method involves growing the host vector system transfected with a plasmid encoding PTPMT1 so as to produce the PTPMT1 molecule in the host and then recovering the PTPMT1 molecules.

The invention also provides a method for treating diseases mediated by PTPMT1, for example Type II diabetes. Accordingly, the invention provides a method for regulating insulin production by PTPMT1 positive cells. The regulation of insulin may confer an increase in insulin levels. The method for regulating insulin production comprises contacting PTPMT1-positive cells with a molecule that recognizes and binds PTPMT1 protein or nucleic acid. An example of molecule that recognizes PTPMT1 is an antibody, Fab or $F(ab')_2$ fragments reactive with PTPMT1. Alternatively, an example of a molecule that recognizes and binds PTPMT1 can be a siRNA molecule of PTPMT1.

Also encompassed by this invention is a method for treating type II diabetes by inhibiting the expression of the PTPMT1 gene comprising contacting PTPMT1 positive cells with an effective amount of a molecule that binds PTPMT1 gene, to inhibit the expression of PTPMT1 gene.

The invention also provides a method for preventing type II diabetes by inhibiting the expression of the PTPMT1 gene comprising contacting PTPMT1 positive cells with a molecule that binds PTPMT1, in an amount effective to inhibit PTPMT1 gene.

Additionally, the invention provides a method for preventing type II diabetes by inhibiting PTPMT1 protein comprising contacting PTPMT1 positive cells with an effective amount of a molecule that binds PTPMT1.

The invention further provides a method for identifying inhibitors of PTPMT1 gene. The method comprises contacting PTPMT1 genes in PTPMT1 positive cells with a molecule of interest and determining whether the contact results in increased insulin production. An increase in insulin production indicates that the molecule is an inhibitor of PTPMT1 gene.

The inventions also provides a method for identifying inhibitors of PTPMT1 protein, the method comprising contacting PTPMT1 protein in PTPMT1 positive cells with a molecule of interest and determining whether the contact results in increased insulin production. An increase in insulin production indicates that the molecule is an inhibitor of PTPMT1 protein. The inhibitor of PTPMT1 may be a small molecule, peptide, or a combination thereof.

The invention also provides a pharmaceutical composition comprising a pharmaceutically effective amount of a PTPMT1 molecule and an acceptable carrier. Additionally a pharmaceutical composition comprising a pharmaceutically effective amount of an antibody that recognizes and binds a PTPMT1 and an acceptable carrier is encompassed by this invention. Also included in this invention is a pharmaceutical composition comprising an effective amount of a recombinant molecule comprising the portion of an anti-PTPMT1 antibody that recognizes a PTPMT1 and a pharmaceutically acceptable carrier. A pharmaceutical composition may also comprise a siRNA of a PTPMT1 protein and a pharmaceutically acceptable carrier.

The invention further provides a composition comprising an immunoconjugate. The immunoconjugate can be the antigen-binding region of the anti-PTPMT1 antibody and a therapeutic agent. The composition is in a pharmaceutically acceptable carrier.

The invention also provides a diagnostic kit that comprises a PTPMT1 protein and a conjugate of a detectable label and a specific binding partner of PTPMT1. A diagnostic kit may comprise a PTPMT1 antibody and a conjugate of a detectable label and a specific binding partner of PTPMT1 antibody. Additionally, a diagnostic kit may also comprise a recombinant molecule, which comprises the antigen-binding region of the antibody of a PTPMT1 and a protein and a conjugate of a detectable label and a specific binding partner of PTPMT1

BRIEF DESCRIPTION OF THE FIGURES

FIG. 5 illustrates the analysis of PLIP as an effector of Akt activity. A shows a proposed model of PI(5)P regulation of Akt activity, adapted from Carricaburu et al. (20). B shows Western blot using anti-FLAG and anti phosphoserine 473-Akt-specific antibodies for wild-type (WT) PLIP, catalytically inactive (C132S) PLIP, or vector control transfected along with FLAG Akt into Chinese hamster ovary-insulin receptor cells and treated with (+) or without (−) insulin and immunoprecipitation with anti-FLAG-agarose beads. In C Drosophila S2 cells were treated with buffer (U) or PLIP or PTEN dsRNA, endogenous Akt was immunoprecipitated and assayed for activity.

FIG. 13 illustrates an example of siRNA of isolated PTPMT1 (SEQ ID NOs:3-4).

FIG. 14 illustrates an example of siRNA of isolated PTPMT1 (SEQ ID NOs:5-6).

FIG. 15 illustrates an example of siRNA of isolated PTPMT1 (SEQ ID NOs:7-8).

FIG. 16 illustrates the cDNA sequence of isolated PTPMT1 from a mouse (SEQ ID NO:44).

FIG. 17 illustrates the amino acid sequence of isolated PTPMT1 from a mouse (SEQ ID NO:40).

FIG. 18 provides one embodiment of a PTPMT1 cDNA (SEQ ID NO:45).

DETAILED DESCRIPTION OF THE INVENTION

Figure 1:
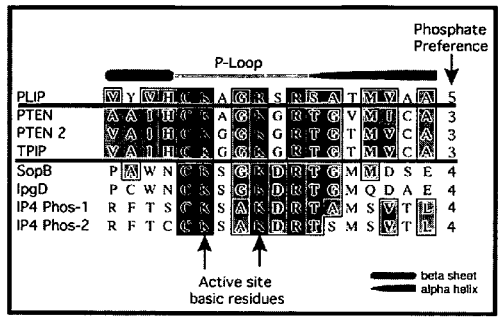
FIG. 1 illustrates the PLIP (also referred to herein as PTPMT1) primary sequence analysis. A shows a primary sequence alignment of the P-loop regions of PTPs possessing a PTEN-like catalytic motif (SEQ ID NOs:12-19). B shows a primary sequence alignment of the P-loop region of various PLIP orthologs organized by ClustalW alignment (SEQ ID NOs:20-38). C shows the primary sequence of murine PLIP (SEQ ID NO:39).

In order that the invention herein described may be more fully understood, the following description is set forth.

As used herein, "phosphatase(s)" are a group of enzymes that catalyze the removal of phosphate groups from their substrate.

As used herein, "kinase(s)" are a group of enzymes that attach phosphate groups to their substrates.

As used herein, "PTP" refers to the protein-tyrosine phosphatase family of phosphatases. "PLIP" refers to PTEN-like phosphatase. PTPMT1 refers to protein tyrosine phosphatase localized to the mitochondrion 1.

As used herein, "PI" is phosphoinositide; "TLC" is thin-layer chromatography; "GST" is glutathione S-transferase; "CHO-IR" is Chinese hamster ovary-insulin receptor; "VHR" is VH-1 related; "TC" is T-cell.

As used herein, "non-protein-tyrosine phosphatase protein sequence" refers to the amino acid sequence that is not coded by members of the PTP family of proteins.

As used herein, the terms "modulate" or "regulate" means to "activate" or "repress" gene transcription and/or expression. To "activate" gene transcription and/or expression means to regulate positively or up-regulate gene transcription and/or expression, whereas to "repress" means to regulate negatively and/or down-regulate gene transcription and expression.

In the experimental disclosure which follows, the following abbreviations apply: M (molar); mM (millimolar); µM (micromolar); nM (nanomolar); mol (moles); mmol (millimoles); µmol (micromoles); nmol (nanomoles); g (grams); mg (milligrams); µg (micrograms); pg (picograms); L (liters); mL (milliliters); ml (milliliters); µL (microliters); cm (centimeters); mm (millimeters); µm (micrometers); nm (nanometers); C (degrees Centigrade).

The invention is directed towards a novel protein-tyrosine phosphatase, PTPMT1, variants and isoforms thereof, nucleic acid molecules encoding them, antibodies that bind them and methods of treating and/or preventing PTPMT1 mediated diseases, such as Type II diabetes. PTPMT1 is a protein which localizes in the cell mitochondria and the absence of PTPMT1 protein increases ATP levels and insulin levels.

PTPMT1 Proteins of the Invention

The invention provides PTPMT1 proteins. In one embodiment, the PTPMT1 protein comprises 193 amino acids as shown in FIG. 17 beginning with methionine at position 1 and ending with asparagine at position 193. In another embodiment, the PTPMT1 protein comprises 174 amino acids as shown in FIG. 17 beginning with leucine at position 20 and ending with asparagine at position 193.

The invention additionally provides a protein comprising a portion of a PTPMT1 protein joined to a non-PTP protein. In one embodiment, the portion of a PTPMT1 protein begins with leucine at position 20 and ends with asparagine at position 193 as shown in FIG. 17. In another embodiment, the portion of a PTPMT1 protein comprises $CX_5R$ (SEQ ID NO:2), wherein C is cysteine; X can be any five of the twenty amino acids, alanine (A), valine (V), leucine (L), isoleucine (I), methionine (M), glycine (G), arginine (R), asparagine (N), glutamine (Q), glutamic acid (E), histidine (H), aspartic acid (D), tryptophan (W), tyrosine (Y), proline (P), lysine (K), cysteine (C), seine (S), threonine (T), and phenylalanine (F); and R is arginine. For example, X includes the five amino acid residues K, S, A, K, and D). Additional embodiments of X include, but are not limited to K, A, G, R, and S; K, A, G, K, and G; K, G, G, K, and G; and K, S, G, K, and D.

PTPMT1 can be expressed and localized using a signal peptide. In one embodiment, the signal peptide comprises amino acids at positions 1-37 or a portion thereof, as shown in FIG. 17. For example the portion of the signal can comprise amino acid positions 20-37, as shown in FIG. 17. The signal peptide may or may not be cleaved after targeting PTPMT1 to the mitochondrion.

The invention additionally provides mutant PTPMT1 proteins. Mutations in PTPMT1 may result from insertion, deletion, frameshift, knockout and/or substitution mutations. Mutant forms of PTPMT1 may increase insulin levels.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

PTPMT1 molecules, derivatives and fragments thereof may be expressed in a soluble form, for example as a fusion protein, wherein PTPMT1 molecules, derivatives and fragments thereof are joined to a non-PTPMT1 sequence. An example of a non-PTPMT1 sequence includes but is not limited to an immunoglobulin sequence. In a further embodiment, the invention provides a PTPMT1 recombinant molecule comprising the region or regions of PTPMT1 that are bound by an anti-PTPMT1 antibody.

PTPMT1 proteins may be embodied in many forms, preferably in an isolated form. As used herein, "isolated murine PTPMT1" or "isolated PTPMT1" refers to a PTPMT1 protein that is expressed and removed from non-PTP protein and/or cellular constituents that are associated with or impair the activity of the PTPMT1 protein. PTPMT1 may be expressed in vivo and/or in vitro (for example in cell lines or by using in vitro transcription translation (IVTT) kits, for example TNT kit from Promega). For isolation and purification of proteins different methods known in the art may be used including, but not limited to, chromatography techniques, such as ion-exchange, gel filtration, hydroxyapatite, hydrophobic, affinity or reversed phase chromatography or chromatofocusing; precipitation techniques, such as chemical precipitation, e.g. with polyethylene glycol, or immunoprecipitation; or electrophoretic techniques, including but not limited to one- or two-dimensional gel electrophoresis and/or isoelectric focusing.

Detection and characterization techniques for proteins include, but are not limited to, spectroscopic methods, such as fluorescence, UV/VIS, infra-red, nuclear magnetic resonance, X-ray, mass spectroscopy, circular dicroism, electron or scanning probe microscopy; chromatographic or electrophoretic techniques, see supra; immunoassays, kinetic assays; and the like.

In an embodiment, the invention provides peptides of PTPMT1 (for example, a peptide comprising amino acid sequence 132-138 of FIG. 17). The peptides exhibit properties of PTPMT1, such as the ability to elicit the generation of antibodies that specifically bind an epitope associated with PTPMT1. Such peptide fragments of the PTPMT1 proteins can be generated using standard peptide synthesis technology and the amino acid sequences of the murine PTPMT1 proteins disclosed herein. Alternatively, recombinant methods can be used to generate nucleic acid molecules that encode a fragment of the PTPMT1 protein. In this regard, the PTPMT1-encoding nucleic acid molecules described herein provide means for generating defined fragments of PTPMT1.

Peptide fragments of PTPMT1 are particularly useful in: generating domain specific antibodies; identifying agents that bind to PTPMT1 or a PTPMT1 domain; identifying cellular factors that bind to PTPMT1 or a PTPMT1 domain; and isolating homologs or other allelic forms of human PTPMT1. PTPMT1 peptides containing particularly interesting structures can be predicted and/or identified using various analytical techniques well known in the art, including, for example, the methods of Chou-Fausman, Garnier-Robson, Kyte-Doolittle, Eisenberg, Karplus-Schultz or Jameson-Wolf analysis, or on the basis of immunogenicity. Peptide fragments are particularly useful in generating subunit specific anti-PTPMT1 antibodies or in identifying cellular factors that bind to PTPMT1.

Nucleic Acid Molecules of the Invention

The invention provides nucleic acid molecules that encode a PTPMT1 protein. The nucleic acid molecule can be a DNA or RNA. In one embodiment, the DNA is an isolated cDNA sequence of PTPMT1, as shown in FIG. 16. In one embodiment, the cDNA comprises a sequence beginning with adenosine at position 1 and ending with adenosine at position 582, as shown in FIG. 16. In another embodiment, the cDNA comprises a sequence beginning with cytosine at position 58 and ending with adenosine at position 582, as shown in FIG. 16.

The nucleic acid molecules described herein enables the isolation of PTPMT1 homologues, alternatively sliced isoforms, allelic variants, and mutant forms of the PTPMT1 protein as well as their coding and gene sequences. In one embodiment, the source of PTPMT1 homologs is mammalian organisms.

Human homologues of PTPMT1, naturally occurring allelic variants of PTPMT1 and genomic PTPMT1 sequences may share a high degree of homology to the mouse PTPMT1 sequences herein described. In general, such nucleic acid molecules will hybridize to the human PTPMT1 sequence under stringent conditions. Such sequences will typically contain at least 70% homology, preferably at least 80%, most preferably at least 90% homology to the mouse PTPMT1 sequence.

Stringent conditions are those that (1) employ low ionic strength and high temperature for washing, for example, 0.015M NaCl/0.0015M sodium nitrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

Antibodies of the Invention

The invention further provides antibodies (e.g., polyclonal, monoclonal, chimeric, and humanized antibodies) that bind to PTPMT1. The most preferred antibodies will selectively bind to PTPMT1 and will not bind (or will bind weakly) to non-PTPMT1 proteins. The most preferred antibodies will specifically bind to PTPMT1. It is intended that the term "specifically bind" means that the antibody predominantly binds to PTPMT1. Anti-PTPMT1 antibodies that are particularly contemplated include monoclonal and polyclonal antibodies as well as fragments thereof (e.g., recombinant proteins) containing the antigen binding domain and/or one or more complement determining regions of these antibodies. These antibodies can be from any source, e.g., rat, dog, cat, pig, horse, mouse or human.

Figure 6:
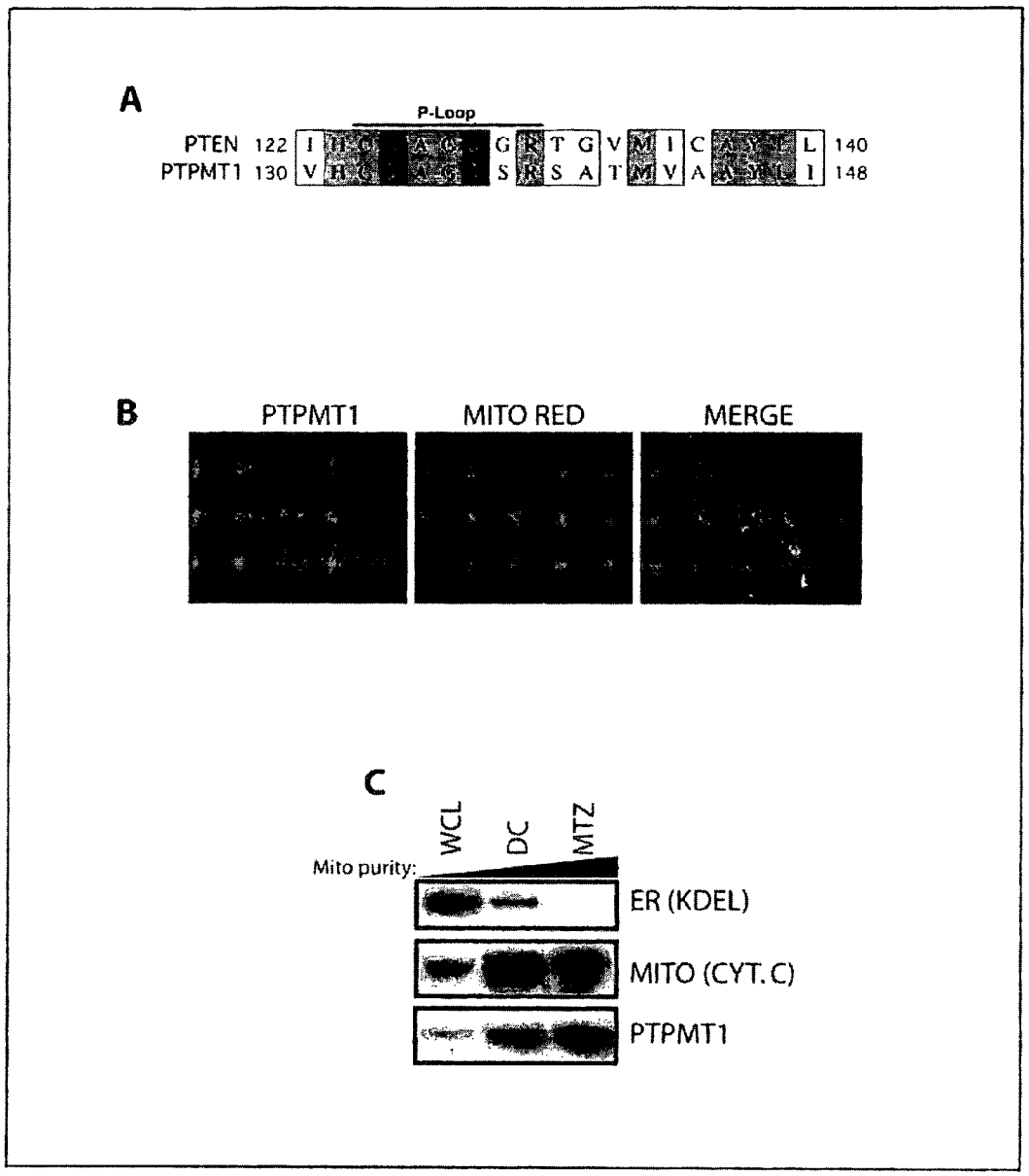
FIG. 6 illustrates that PTPMT1 is a PTEN-like phosphatase localized to mitochondria. A shows the primary sequence alignment of the active site region of mouse PTPMT1 and PTEN using the Clustal W algorithm (SEQ ID NOs:48-49). B shows that PTPMT1 localizes to the mitochondria and C shows a SDS-PAGE and immunoblot analysis of rat liver whole cell lysate (WCL), differential centrifugation purified mitochondria (DC), and metrizamide gradient purified mitochondria (MTZ) using KDEL antibody for ER, cytochrome c antibody for mitochondria, and anti-PTPMT1 antibody.

In one embodiment, the PTPMT1 antibodies specifically bind to the active site of PTPMT1, for example, the P loop of PTPMT1 (FIG. 6). In other embodiments, the PTPMT1 antibodies specifically bind to other domains of a PTPMT1 protein or precursor, such as a portion of the N-terminal region, the middle region, or the C-terminal region. In one embodiment, in PTPMT1 proteins having amino acids 1-193 of FIG. 17, the N-terminal region can comprise amino acids 1-64 of FIG. 17, the middle region can comprise amino acids 65-129 of FIG. 17, and the C-terminal can comprise amino acids 130-193 of FIG. 17. In another embodiment, in PTPMT1 proteins having the amino acid sequence 20-193 of FIG. 17, the N-terminal region can comprise amino acids 20-78, the middle region can comprise amino acids 79-137 and the C-terminal region can comprise amino acids 138-193. As will be understood by those skilled in the art, the regions or epitopes of a PTPMT1 protein to which an antibody is directed may vary with the intended application. For example, antibodies intended for use in an immunoassay for the detection of membrane-bound PTPMT1 on viable pancreatic cells should be directed to an accessible epitope on membrane-bound PTPMT1. Antibodies that recognize other epitopes may be useful for the identification of PTPMT1 within damaged or dying cells, for the detection of secreted PTPMT1 proteins or fragments thereof. The invention also encompasses antibody fragments that specifically recognize a PTPMT1 protein. As used herein, an antibody fragment is defined as at least a portion of the variable region of the immunoglobulin molecule that binds to its target, i.e., the antigen binding region. Some of the constant region of the immunoglobulin may be included.

In another embodiment, the invention provides various immunological assays useful for the detection of PTPMT1 protein. Such assays generally comprise one or more PTPMT1 antibodies capable of recognizing and binding a PTPMT1 protein, and include various immunological assay formats well known in the art, including but not limited to various types of precipitation, agglutination, complement fixation, radioimmunoassays (RIA), enzyme-linked immunosorbent assays (ELISA), enzyme-linked immunofluorescent assays (ELIFA) (H. Liu et al. Cancer Research 58: 4055-4060 (1998), immunohistochemical analysis and the like.

PTPMT1 antibodies may also be used in methods for purifying PTPMT1 proteins and peptides and for isolating PTPMT1 homologues and related molecules. For example, in one embodiment, the method of purifying a PTPMT1 protein comprises incubating a PTPMT1 antibody, which has been coupled to a solid matrix, with a lysate or other solution containing PTPMT1 under conditions which permit the PTPMT1 antibody to bind to PTPMT1; washing the solid matrix to eliminate impurities; and eluting the PTPMT1 from the coupled antibody. Additionally, PTPMT1 antibodies may be used to isolate PTPMT1 positive cells using cell sorting and purification techniques. Other uses of the PTPMT1 antibodies of the invention include generating anti-idiotypic antibodies that mimic the PTPMT1 protein, e.g., a monoclonal anti-idiotypic antibody reactive with an idiotype on any of the monoclonal antibodies embodied by the invention.

Various methods for the preparation of antibodies are well known in the art. For example, antibodies may be prepared by immunizing a suitable mammalian host using a PTPMT1 protein, peptide, or fragment, in isolated or immunoconjugated form (Harlow, Antibodies, Cold Spring Harbor Press, NY (1989)). In addition, fusion proteins of PTPMT1 may also be used, such as a PTPMT1 GST-fusion protein. Cells expressing or overexpressing PTPMT1 may also be used for immunizations. Similarly, any cell engineered to express PTPMT1 may be used. This strategy may result in the production of monoclonal antibodies with enhanced capacities for recognizing endogenous PTPMT1.

Another embodiment of the invention includes chimeric antibodies which are immunoglobulin molecules that comprise a human and non-human portion. The antigen combining region (variable region) of a chimeric antibody can be derived from a non-human source (e.g. murine) and the constant region of the chimeric antibody which confers biological effector function to the immunoglobulin can be derived from a human source. The chimeric antibody should have the antigen binding specificity of the non-human antibody molecule and the effector function conferred by the human antibody molecule.

In general, the procedures used to produce chimeric antibodies can involve the following steps:
a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;
b) cloning the gene segments encoding the constant region or desired part thereof;
c) ligating the variable region with the constant region so that the complete chimeric antibody is encoded in a form that can be transcribed and translated;
d) ligating this construct into a vector containing a selectable marker and gene control regions such as promoters, enhancers and poly(A) addition signals;
e) amplifying this construct in bacteria;
f) introducing this DNA into eukaryotic cells (transfection) most often mammalian lymphocytes;
g) selecting for cells expressing the selectable marker;
h) screening for cells expressing the desired chimeric antibody; and
k) testing the antibody for appropriate binding specificity and effector functions.

Antibodies of several distinct antigen binding specificities have been manipulated by these protocols to produce chimeric proteins (e.g. anti-TNP: Boulianne et al., *Nature* 312: 643 (1984); and anti-tumor antigens: Sahagan et al., *J. Immunol.* 137:1066 (1986)). Likewise, several different effector functions have been achieved by linking new sequences to those encoding the antigen binding region. Some of these include enzymes (Neuberger et al., *Nature* 312:604 (1984)), immunoglobulin constant regions from another species and constant regions of another immunoglobulin chain (Sharon et al., *Nature* 309:364 (1984); Tan et al., *J. Immunol.* 135:3565-3567 (1985)). Additionally, procedures for modifying antibody molecules and for producing chimeric antibody molecules using homologous recombination to target gene modification have been described (Fell et al., *Proc. Natl. Acad. Sci. USA* 86:8507-8511 (1989)).

The amino acid sequence of PTPMT1 presented herein may be used to select specific regions of the PTPMT1 protein for generating antibodies. For example, hydrophobicity and hydrophilicity analyses of the PTPMT1 amino acid sequence may be used to identify hydrophilic regions in the PTPMT1 structure. Regions of the PTPMT1 protein that show immunogenic structure, as well as other regions and domains, can readily be identified using various other methods known in the art, such as Chou-Fausman, Garnier-Robson, Kyte-Doolittle, Eisenberg, Karplus-Schultz or Jameson-Wolf analysis. Fragments containing these residues are particularly suited in generating specific classes of anti-PTPMT1 antibodies.

Methods for preparing a protein for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PTPMT1 immunogen is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the PTPMT1 protein or PTPMT1 fragment. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonal antibodies of the invention or the polyclonal antisera (e.g., Fab, F(ab')$_2$, Fv fragments, fusion proteins) which contain the immunologically significant portion (i.e., a portion that recognizes and binds PTPMT1) can be used as antagonists, as well as the intact antibodies. Humanized antibodies directed against PTPMT1 are also useful. As used herein, a humanized PTPMT1 antibody is an immunoglobulin molecule which is capable of binding to PTPMT1 and which comprises a FR region having substantially the amino acid sequence of a human immunoglobulin and a CDR having substantially the amino acid sequence of non-human immunoglobulin or a sequence engineered to bind PTPMT1. Methods for humanizing murine and other non-human antibodies by substituting one or more of the non-human antibody CDRs for corresponding human antibody sequences are well known (see for example, Jones et al., 1986, Nature 321: 522-525; Riechmnan et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Use of immunologically reactive fragments, such as the Fab, Fab', or F(ab')$_2$ fragments is often preferable, especially in a therapeutic context, as these fragments are generally less immunogenic than the whole immunoglobulin. Further, bi-specific antibodies specific for two or more epitopes may be generated using methods generally known in the art. Further, antibody effector functions may be modified so as to enhance the therapeutic effect of PTPMT1 antibodies on cancers. For example, cysteine residues may be engineered into the Fc region, permitting the formation of interchain disulfide bonds and the generation of homodimers which may have enhanced capacities for internalization, ADCC and/or complement-mediated cell killing (see, for example, Caron et al., 1992, J. Exp. Med. 176: 1191-1195; Shopes, 1992, J. Immunol. 148: 2918-2922). Homodimeric antibodies may also be generated by cross-linking techniques known in the art (e.g., Wolff et al., Cancer Res. 53: 2560-2565). In an embodiment, the invention provides pharmaceutical compositions having the monoclonal antibodies or anti-idiotypic monoclonal antibodies of the invention.

Alternatively, methods for producing fully human monoclonal antibodies, include phage display and transgenic methods, are known and may be used for the generation of human mAbs (for review, see Vaughan et al., 1998, Nature Biotechnology 16: 535-539). For example, fully human anti-PTPMT1 monoclonal antibodies may be generated using cloning technologies employing large human Ig gene combinatorial libraries (i.e., phage display)(Griffiths and Hoogenboom), building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human anti-PTPMT1 monoclonal antibodies may also be produced using transgenic mice engineered to contain human immunoglobulin gene loci (Jakobovits, 1998, Exp. Opin. Invest. Drugs 7(4): 607-614). This method avoids the in vitro manipulation required with phage display technology and efficiently produces high affinity authentic human antibodies.

The antibody or fragment thereof of the invention may be labeled with a detectable marker or conjugated to a second molecule, such as a therapeutic agent (e.g., a cytotoxic agent) thereby resulting in an immunoconjugate. For example, the therapeutic agent includes, but is not limited to, an anti-tumor drug, a toxin, a radioactive agent, a cytokine, a second antibody or an enzyme. Further, the invention provides an embodiment wherein the antibody is linked to an enzyme that converts a prodrug into an active form. The immunoconjugate may be used for targeting a second molecule to a PTPMT1 positive cell (Vitetta, E. S. et al., 1993, Immunotoxin therapy, in DeVita, Jr., V. T. et al., eds, Cancer: Principles and Practice of Oncology, 4th ed., J.B. Lippincott Co., Philadelphia, 2624-2636).

Techniques for conjugating or joining therapeutic agents to antibodies are well known (see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", *Immunol. Rev.,* 62:119-58 (1982)).

Method for Producing PTPMT1 of the Invention

The invention also provides a method for producing PTPMT1 molecules, derivatives and/or fragments thereof. The PTPMT1 protein molecules, derivative and/or fragments thereof may be naturally occurring, recombinant or chemically synthesized. These may be modified by one or more purification tags, including, but not limited to, His6, epitope (e.g., myc, V5, FLAG or soft-epitope), streptavidin, biotin, avidin, tetracysteine, calmodulin-binding protein, elastin-like peptide, fusion protein (e.g., glutathione-S-transferase, maltose binding protein, cellulose-binding domain, thioredoxin, NusA or mistin), chitin-binding domain, GFP, alkaline phosphatase, cutinase, $O^6$-alkylguanine alkyltransferase (AGT), or halo tag.

This method involves growing the host-vector system transfected with a plasmid encoding PTPMT1, derivatives or fragments thereof, so as to produce the PTPMT1 molecules, derivatives or fragments thereof, in the host and then recovering the PTPMT1 molecules, derivatives or fragments thereof. The techniques for assembling and expressing DNA encoding the amino acid sequences corresponding to PTPMT1 protein, derivatives and fragments thereof, e.g. synthesis of oligonucleotides, PCR, transforming cells, constructing vectors, expression systems, and the like are well-established in the art, and most practitioners are familiar with the standard resource materials for specific conditions and procedures. The nucleotide sequences encoding the amino acid sequences corresponding to the PTPMT1 protein, derivatives or fragments thereof, may be expressed in a variety of systems known in the art. The cDNA may be excised by suitable restriction enzymes and ligated into suitable prokaryotic or eukaryotic expression vectors for such expression.

Specifically, construction of suitable vectors containing the desired gene coding and control sequences employs standard ligation and restriction techniques, which are well understood in the art (see Maniatis et al., in *Molecular Cloning*: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 μg of plasmid or DNA sequences is cleaved by one unit of enzyme in about 20 μl of buffer solution. Typically, an excess of restriction enzyme is used to insure complete digestion of the DNA substrate.

Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499-560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM $MgCl_2$, 6 mM DTT and 5-10 μM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10-50 μl volumes under the following standard conditions and temperatures using T4 DNA ligase. Ligation protocols are standard (D. Goeddel (ed.) Gene Expression Technology: Methods in Enzymology (1991)).

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

The recombinant protein may be expressed in a prokaryotic, yeast, insect, plant or mammalian system. Examples of well known prokaryotic (bacterial) expression systems are *E. coli* (e.g. BL21, BL21 (DE3), XL1, XL1 Blue, DH5α or DH10B cell strains) and *B. subtilis*. Yeast cells include, but are not limited to, *P. pastoris, K. lactis, S. cerevisiae, S. pombe, Y. lipolyt* and *K. marxianus*. Suitable mammalian cell lines may be, among others, CHO, HEK 293 BHK, NS0, NS1, SP2/0. Insect cell lines may include, for example, *Drosophila, Aedes aegypti* mosquitoe, Sf21, Sf9, and T.ni cell lines. The isolated protein may comprise, depending of the expression system, different posttranslational modifications of amino acids, such as acetate groups, phosphate groups, various lipids and carbohydrates, changed chemical nature of an amino acid (e.g. citrullination) or structural changes, like disulfide bridges.

Suitable vectors include viral vector systems e.g. ADV, RV, and AAV (R. J. Kaufman "Vectors used for expression in mammalian cells" in *Gene Expression Technology*, edited by D. V. Goeddel (1991).

Many methods for inserting functional DNA transgenes into cells are known in the art. For example, non-vector methods include nonviral physical transfection of DNA into cells; for example, microinjection (DePamphilis et al., *BioTechnique* 6:662-680 (1988)); liposomal mediated transfection (Felgner et al., *Proc. Natl. Acad. Sci. USA*, 84:7413-7417 (1987), Felgner and Holm, *Focus* 11:21-25 (1989) and Felgner et al., *Proc. West. Pharmacol. Soc.* 32: 115-121 (1989)) and other methods known in the art.

Screening Assays of the Invention

Another aspect of the invention relates to assays and methods that can be used to identify and detect molecules that bind PTPMT1. As used herein, "bound-PTPMT1" refers to PTPMT1 that is bound to a binding molecule. Examples of binding molecules include but are not limited to peptides, small molecules, antibodies, DNA, RNA and/or siRNA. Binding molecules may be naturally occurring or synthetic. In one embodiment, bound-PTPMT1 increase insulin levels. Assays for PTPMT1 activity (e.g., insulin production, ATP production) using a PTPMT1 protein are suitable for use in high through-put screening methods.

In one embodiment, the assay comprises mixing PTPMT1 with a binding molecule or cellular extract. After mixing under conditions that allow association of PTPMT1 with the binding molecule or a component of the cellular extract, the mixture is analyzed to determine if the binding molecule/component is bound to PTPMT1. Binding molecules/components are identified as being able to bind to PTPMT1. The effect of PTPMT1 binding molecules, bound to PTPMT1 may be assessed by assaying for insulin production, using high-through-put screening methods. Accordingly, agonists and antagonists of PTPMT1 activity can be identified.

Alternatively, targets that bind to a PTPMT1 protein can be identified using a yeast two-hybrid system (Fields, S. and Song, O. (1989), Nature 340:245-246) or using a binding-capture assay (Harlow, supra). In the yeast two hybrid system, an expression unit encoding a fusion protein made up of one subunit of a two subunit transcription factor and the PTPMT1 protein is introduced and expressed in a yeast cell. The cell is further modified to contain (1) an expression unit encoding a detectable marker whose expression requires the two subunit transcription factor for expression and (2) an expression unit that encodes a fusion protein made up of the second subunit of the transcription factor and a cloned segment of DNA. If the cloned segment of DNA encodes a protein that binds to the PTPMT1 protein, the expression results in the interaction of the PTPMT1 and the encoded protein. This brings the two subunits of the transcription factor into binding proximity, allowing reconstitution of the transcription factor. This results in the expression of the detectable marker. The yeast two hybrid system is particularly useful in screening a library of cDNA encoding segments for cellular binding partners of PTPMT1. The effect of the targets on PTPMT1 activity may be assessed by assaying for insulin production.

PTPMT1 proteins which may be used in the above assays include, but are not limited to, an isolated PTPMT1 protein, a fragment of a PTPMT1 protein, a cell that has been altered to express a PTPMT1 protein, or a fraction of a cell that has been altered to express a PTPMT1 protein. Further, the PTPMT1 protein can be the entire PTPMT1 protein or a defined fragment of the PTPMT1 protein. It will be apparent to one of ordinary skill in the art that so long as the PTPMT1 protein can be assayed for agent binding, e.g., by a shift in molecular weight or activity, the present assay can be used.

The method used to identify whether binding molecule and/or cellular component binds to a PTPMT1 protein will be based primarily on the nature of the PTPMT1 protein used. For example, a gel retardation assay can be used to determine whether an agent binds to PTPMT1 or a fragment thereof. Alternatively, immunodetection and biochip technologies can be adopted for use with the PTPMT1 protein. A skilled artisan can readily employ numerous art-known techniques for determining whether a particular agent binds to a PTPMT1 protein. Further, the effects of binding molecules and/or cellular components on PTPMT1 activity can be determined by detecting insulin production.

Binding molecules and cellular components can be further tested for the ability to modulate the activity of a PTPMT1 protein using a cell-free assay system or a cellular assay system. As the activities of the PTPMT1 protein become more defined (for example, activities in addition to modulating insulin production), functional assays based on the identified activity can be employed.

As used herein, an agent is said to antagonize PTPMT1 activity when the agent reduces PTPMT1 activity. The preferred antagonist will selectively antagonize PTPMT1, not affecting any other cellular proteins. Further, the preferred antagonist will reduce PTPMT1 activity by more than 50%, more preferably by more than 90%, most preferably eliminating all PTPMT1 activity. Reduction of PTPMT1 activity may result in increased insulin production.

As used herein, an agent is said to agonize PTPMT1 activity when the agent increases PTPMT1 activity. The preferred agonist will selectively agonize PTPMT1, not affecting any other cellular proteins. Further, the preferred antagonist will increase PTPMT1 activity by more than 50%, more preferably by more than 90%, most preferably more than doubling PTPMT1 activity.

Binding molecules that are assayed in the above method can be randomly selected or rationally selected or designed. As used herein, a binding molecule is said to be randomly selected when the binding molecule is chosen randomly without considering the specific sequences of the PTPMT1 protein. An example of randomly selected binding molecule is the use of a chemical library or a peptide combinatorial library, or a growth broth of an organism or plant extract.

As used herein, a binding molecule is said to be rationally selected or designed when the binding molecule is chosen on a nonrandom basis that takes into account the sequence of the target site and/or its conformation in connection with the binding molecule's action. Binding molecule can be rationally selected or rationally designed by utilizing the peptide sequences that make up the PTPMT1 protein. For example, a rationally selected peptide agent can be a peptide whose amino acid sequence is identical to a fragment of a PTPMT1 protein.

The binding molecule can be, for example, peptides, small molecules, and vitamin derivatives, as well as carbohydrates. A skilled artisan can readily recognize that there is no limit as to the structural nature of the agents used in the present screening method. One class of binding molecule of the present invention is an siRNA of PTPMT1. Examples of suitable siRNA include, but are not limited to, the sequence GUCUGUGGAUGACAAAGAAtt (SEQ ID NO:3) or UUCUUUGUCAUCCACAGACtt (SEQ ID NO:4); the sequence GCCAGUUGGAAAUUCUCAATT (SEQ ID NO:5) or UUGAGAAUUUCCAACUGGCTG (SEQ ID NO:6); the sequence GUUGGAAAUUCUCAAAGAGTT (SEQ ID NO:7) or CUCUUUGAGAAUUUCCAACTG (SEQ ID NO:8); or combinations thereof.

In an embodiment, binding molecules are small peptides whose amino acid sequences are chosen based on the amino acid sequence of the PTPMT1 protein. Small peptides can serve as competitive inhibitors of PTPMT1 protein assembly.

Peptide agents can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

In an embodiment of the invention, antibodies against PTPMT1 function as binding molecules described above. Anti-PTPMT1 antibodies can be used to modulate PTPMT1 activity. In one embodiment, modulation of PTPMT1 activity by anti-PTPMT1 antibodies results in increased insulin levels.

The cellular extracts embodied in the methods of the present invention can be, as examples, aqueous extracts of cells or tissues, organic extracts of cells or tissues or partially purified cellular fractions. A skilled artisan can readily recognize that there is no limit as to the source of the cellular extract used in the screening method of the present invention.

The invention further provides a method for regulating insulin production. In one embodiment, rendering PTPMT1 inactive or unavailable for function regulates insulin production. For example, insulin production may be regulated by contacting PTPMT1-positive cells with an antibody, Fab or F(ab')$_2$ fragments reactive with PTPMT1. Antibodies and fragments thereof, reactive with PTPMT1 may render PTPMT1 inactive or unavailable for function, thereby increasing levels of insulin.

In another embodiment, decreasing the amount of PTPMT1 regulates insulin production. For example, contacting PTPMT1-positive cells with a nucleic acid molecule, such as siRNA, would decrease the amount of PTPMT1 produced, thereby increasing insulin levels. In one embodiment, the siRNA molecule comprises a sequence GUCUGUGAUGACAAAGAAtt (SEQ ID NO:3) or UUCUUUGUCAUCCACAGACtt (SEQ ID NO:4). In another embodiment, siRNA molecule comprises a sequence GCCAGUUGGAAAUUCUCAATT (SEQ ID NO:5) or UUGAGAAUUUCCAACUGGCTG (SEQ ID NO:6). In a further embodiment, the siRNA molecule comprises a sequence GUUGGAAAUUCUCAAAGAGTT (SEQ ID NO:7) or CUCUUUGAGAAUUUCCAACTG (SEQ ID NO:8).

The invention provides a method for treating and/or preventing diseases mediated by PTPMT1 cell interactions. For example, one of the treatments for type II diabetes involves increasing insulin production. The method comprises administering to a subject an effective amount of a molecule that binds PTPMT1, thereby decreasing the levels of PTPMT1 and increasing insulin production. Examples of molecules that bind PTPMT1 include but are not limited to antibodies and nucleic acid molecules, such as siRNA.

The invention further provides a method for identifying inhibitors of PTPMT1 gene or PTPMT1 protein. The method comprises contacting PTPMT1 gene or PTPMT1 protein in PTPMT1 positive cells with a molecule of interest and subsequently determining whether the contact results in increased insulin production. An increase in insulin production is indicative that the molecule is an inhibitor of PTPMT1 gene or PTPMT1 protein. Molecules that are inhibitors of PTPMT1 include but are not limited to small molecules, nucleic acids, peptides, antibodies, or a combination thereof.

Also encompassed by the invention is a diagnostic kit comprising (a) the PTPMT1 protein, derivative or fragment thereof, or an anti-PTPMT1 antibody or a PTPMT1 recombinant protein, and (b) a conjugate of a detectable label and a specific binding partner of (a). The labels are selected from a group comprising enzymes, chromophores and fluorescers.

The invention provides a pharmaceutical composition comprising an effective amount of PTPMT1 and a pharmaceutically acceptable carrier. The invention further provides a pharmaceutical composition comprising an antibody that binds PTPMT1 protein, derivative or fragment thereof and a pharmaceutically acceptable carrier. Additionally, a pharmaceutical composition comprises a siRNA of PTPMT1 and a pharmaceutically acceptable carrier. A pharmaceutical composition may also comprise one or more binding molecules of PTPMT1 identified by the methods of the invention, and a pharmaceutically acceptable carrier.

The pharmaceutical compositions preferably include suitable carriers and adjuvants which include any material which when combined with the molecules of the invention (e.g., molecules that recognize and bind PTPMT1 protein or DNA, such as an antibody or siRNA) retain the molecule's activity, and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g. sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The subjects treated by the present invention include mammalian subjects, including, human, monkey, ape, dog, cat, cow, horse, goat, pig, rabbit, mouse and rat.

Examples of cell lines that may be used to practice the claimed invention includes but is not limited to INS-1 and derivatives thereof.

The modes of administration encompassed by the methods of the invention include but are not limited to intravenous, intramuscular, intraperitoneal, oral, inhalation and subcutaneous methods, as well as implantable pump, continuous infusion, gene therapy, liposomes, suppositories, topical contact, vesicles, capsules, biodegradable polymers, hydrogels, controlled release patch and injection.

Another aspect of the invention provides transgenic non-human mammals comprising PTPMT1 nucleic acids. For example, in one application, PTPMT1-deficient non-human animals can be generated using standard knock-out procedures to inactivate a PTPMT1 homologue or, if such animals are non-viable, inducible PTPMT1 homologue antisense molecules can be used to regulate PTPMT1 homologue activity/expression. Alternatively, an animal can be altered so as to contain a human PTPMT1-encoding nucleic acid molecule or an antisense-PTPMT1 expression unit that directs the expression of PTPMT1 protein or the antisense molecule in a tissue specific fashion. In such uses, a non-human mammal, for example a mouse or a rat, is generated in which the expression of the PTPMT1 homologue gene is altered by inactivation or activation and/or replaced by a human PTPMT1 gene. This can be accomplished using a variety of art-known procedures such as targeted recombination. Once generated, the PTPMT1 homologue deficient animal, the animal that expresses PTPMT1 (human or homologue) in a tissue specific manner, or an animal that expresses an antisense molecule can be used to (1) identify biological and pathological processes mediated by the PTPMT1 protein, (2) identify proteins and other genes that interact with the PTPMT1 proteins, (3) identify agents that can be exogenously supplied to overcome a PTPMT1 protein deficiency and (4) serve as an appropriate screen for identifying mutations within the PTPMT1 gene that increase or decrease activity.

For example, it is possible to generate transgenic mice expressing the human minigene encoding PTPMT1 in a tissue specific-fashion and test the effect of over-expression of the protein in tissues and cells that normally do not contain the PTPMT1 protein. This strategy has been successfully used for other genes, namely bcl-2 (Veis et al. Cell 1993 75:229). Such an approach can readily be applied to the PTPMT1 protein/gene and can be used to address the issue of a potential beneficial or detrimental effect of the PTPMT1 proteins in a specific tissue.

EXAMPLES

Example 1

Applicants report the first example of a mammalian phosphatase utilizing PI(5)P as its preferred substrate.

Materials and Methods

Expression and Purification of PLIP

Recombinant murine PLIP was expressed as a fusion protein with N-terminal GST and 6-His tags in *Escherichia coli* BL21 (DE3) CodonPlus RIL cells (Stratagene). The expression construct was assembled by ligating a PCR product encoding full-length PLIP into the 5'-EcoR1 and 3'-Xho1 sites of a modified pET41 vector (pSJ6), kindly provided by Zhaohui Xu (University of Michigan). One liter Bacterial cultures were grown @ 37° C. in 2XYT media possessing Chloramphenicol (34 µg/ml) and Kanamycin (50 µg/ml) to an OD of 0.5-0.7. Cultures were then chilled on ice for 20 min, supplied with fresh antibiotics, induced with IPTG to a final concentration of 0.4 mM, and allowed to grow overnight @ 25° C., as previously described (Taylor and Dixon, 2003). All subsequent steps were performed @ 4° C. The cultures were pelleted by spinning @ 6000 rpm for 10 min in a Sorvall GSA rotor, resuspended in 30 ml of buffer (20 mM Imidazole, 50 mM Tris pH 7.4, 300 mM NaCl) with Complete protease inhibitors (Roche), and lysed via French Press. Insoluble material was removed by centrifugation @ 50,000 rpm for 30 min. The fusion protein was purified from the soluble supernatant first over $Ni^{2+}$ agarose beads, and then by successive separation on Superdex 75 and 200 gel filtration columns (Amersham). The resulting protein was concentrated, flash frozen in liquid nitrogen, and stored @−80° C. in 25% glycerol, 2 mM EDTA, and 2 mM DTT until use.

Fluorescent Phosphoinositide Assays

Fluorescent PI, TLC, and malachite green assays were performed as recently described (Taylor and Dixon, 2003). Eighteen microliters of assay buffer (50 mM ammonium acetate (pH 5.5), 0.1% (v:v) 2-mercaptoethanol (Sigma)) containing 1 µg of a Di-$C_6$-NBD6-phosphoinositide (Echelon) were prewarmed at 37° C. for 5 min. Reactions were initiated by the addition of 2 µl of 0.1 µg/µl GST-PLIP diluted in assay buffered containing 1.0 mg/ml gelatin. Assays were quenched after 2.0 min by the addition of 100 µl of acetone and dried in a Speed Vac at medium heat.

Thin Layer Chromatography

Whatman K6 silica gel plates (Fisher) were soaked in a 1.2% solution of potassium oxalate, air-dried in a fume hood for 10 min, and placed in a baking oven for 1 hr @ 180° F. under vacuum. The dried products of the fluorescent phosphoinositide assays were resuspended in 20 µl of MeOH/2-propanol/glacial acetic acid (5:5:2) and spotted onto the TLC plate. The plate was dried for 10 min in a fume hood and developed in $CHCl_3$/MeOH/acetone/glacial acetic acid/water (70:50:20:20:20). The plate was again dried in a fume hood and visualized on a Biorad DNA gel UV illuminator.

Malachite Green Assays

Di-$C_8$ phosphoinosites (Echelon) and Dioleoyl-phosphatidylserine (Sigma) were dried together in a Speed Vac and resuspended via sonication in 18 µl assay buffer (100 mM sodium acetate, 50 mM bis-Tris, 50 mM Tris (pH 5.5), 10 mM DTT) to final concentrations of 50 µM and 500 µM, respectively. After prewarming at 37° C. for 5 min, reactions were initiated by the addition of 20 to 2000 ng of GST-PLIP diluted in assay buffer containing 1.0 mg/ml gelatin. Reactions were quenched after 5-30 min by the addition of 20 µl 0.1 M N-ethylmaleimide, and spun at 18,000×g for 10 min to sediment the lipid aggregates. Twenty-five microliters of the supernatant was added to 50 µl of malachite green reagent and vortexed. Samples were allowed to sit for 40 minutes for color development before measuring absorbance at 620 nM. Inorganic phosphate release was quantitated by comparison to a standard curve of $KH_2PO_4$ in $dH_2O$.

Phosphatase Assays

Assays using radiolabeled protein substrates or pNPP were carried in assay buffer containing 50 mM sodium acetate, 25 mM bis-Tris, 25 mM Tris, and 2 mM DTT at pH 5.5 (GST-PLIP), 6.0 (VHR), or 7.0 (TC-PTP), at 30° C. Radiolabeled proteins and pNPP were prepared and assayed as previously reported (Taylor et al., 1997).

Tissue Expression

Tissue distribution of PLIP was analyzed both with a FirstChoice Northern Blot System (Ambion) using a random-primed $^{32}$P-labeled probe, as well by PCR analysis using a mouse multiple tissue cDNA panel (Clontech) with the following primers:

```
                                              (SEQ ID NO: 9)
5'-CCACCGCATCGACCACACGGTTCTGC-3' (fwd), (SEQ ID NO: 10)
5'-CCTCCTCTGGGCTCCAGTTGTGTACCTGAATCAG-3' (rev).
```

Analysis of Akt Activity in CHO-IR Cells

CHO-IR cells were maintained at 37° C. and 5% $CO_2$ in alpha Minimum Essential Media (Gibco) supplemented with 10% FBS, 50 U/ml each of penicillin and streptomycin, and 50 µg/ml Genetecin. Cells were transfected with FLAG-Akt (kindly provided by Dr. Anne Vojtek, University of Michigan), and either vector, wild-type PLIP-V5, or C132S PLIP-V5 in a 1:10 ratio using Fugene (Roche) according to the manufacturer's recommended protocol. Twenty-four hours post transfection, cells were serum starved overnight followed by treatment±10 nM insulin for 5 minutes. Cells were then lysed and the Akt immunoprecipitated using anti-FLAG agarose (Sigma). Samples for all six conditions were Western blotted for Akt (anti-FLAG (Sigma)), phospho S473 Akt (Cell Signaling Technology), or PLIP (anti-V5 (Invitrogen)).

RNAi in *Drosophila* S2 Cells

S2 cells were grown in 1× Schneider's *Drosophila* media (GIBCO) supplemented with 10% FBS, 50 µg/ml streptomycin in 75-cm$^2$ T-flasks (Starstedt) at room temperature. DsRNA for RNAi experiments was produced as used to treat S2 cells as previously reported in detail (Worby et al., 2001). Briefly, dsRNA was added to a final concentration of approximately 37 nM to 1×10$^6$ cells in each well of a six well plate followed by vigorous agitation. Following a thirty minute incubation at 25° C., 2 ml of 1× Schneider's media with FBS. After 3 days at 25° C., mRNA was isolated using Roche's mRNA capture kit and analyzed by gel electrophoresis. AKT immunoprecipitations and activity assays were performed as described previously (Clemens et al., 2000).

Results and Discussion

Identification of PLIP as a PTEN-Like Phosphatase

Elucidation of the crystal structure of PTEN revealed the importance of the conserved active site lysine residues (K125, K128) in establishing a negatively charged catalytic pocket conducive to the binding of its preferred substrate, PI(3,4,5) P3 (Lee et al., 1999). In an attempt to identify additional phosphatases possessing this motif, PSI-BLAST analyses were conducted using the PTEN phosphatase domain as a query (Altschul et al., 1990; Altschul et al., 1997). Applicants subsequently identified a predicted protein, (NCBI accession: XP_374879), that possessed the PTEN-like active site CKAGRSR (SEQ ID NO:11). Using the murine ortholog of this protein, multiple PSI-BLAST and TBLASTN searches were conducted against the non-redundant and EST databases. Through this analysis, over 60 orthologs of a protein now called PLIP. Included in these results is an ortholog from the eubacterium *Pirellula* sp. strain 1, whose defining characteristics include an intracellular membrane and various eukaryotic-like lipids (Lindsay et al., 2001; Glockner et al., 2003). The active site region of PLIP shows remarkable evolutionary conservation, exhibiting greater than 70% identity/80% similarity in orthologs from 4 different phylogenetic kingdoms. Such conservation supports the notion that residues within this region are critical for proper enzyme function, most likely in establishing substrate specificity.

FIG. 1 illustrates the PLIP primary sequence analysis. A shows a primary sequence alignment of the P-loop regions of PTPs possessing a PTEN-like catalytic motif. Catalytic cysteine and arginine residues are highlighted in red, and active site basic residues are in blue. The phosphate position of the inositol ring dephosphorylated by each enzyme is indicated on the right. B shows a primary sequence alignment of the P-loop region of various PLIP orthologs organized by ClustalW alignment. The cladogram at the left shows the evolutionary progression of PLIP orthologs through four kingdoms (Eubacteria, *Pirellula* sp.; Protista, *D. discoideum*; Plantae, *P. taeda* through *H. magnipapillata*; Animalia, *E. granulosus* through *H. sapiens*). "PROT" denotes sequences derived from characterized proteins or predicted proteins from fully sequenced genomes, "EST" denotes sequences derived from expressed sequence tags. NCBI accession numbers are given at right. (Note: cladogram not to scale.) FIG. 1C shows the primary sequence of murine PLIP. Shaded region, beginning with green-boxed-start methionine, indicates the sequence of the clone used in this study. The catalytic P-loop region is highlighted in red.

PLIP Exhibits PI(5)P Phosphatase Activity

The murine ortholog of PLIP (FIG. 1C), was cloned into a GST bacterial expression vector, expressed, and purified to near homogeneity. The predicted amino acid sequence of this ortholog has an extended N-terminus (residues 1-69, FIG. 1C). However, as this region was not found in any of the more than 60 other PLIP orthologs, it was omitted from the final GST-PLIP construct used for the biochemical characterization of PLIP.

Figure 2:
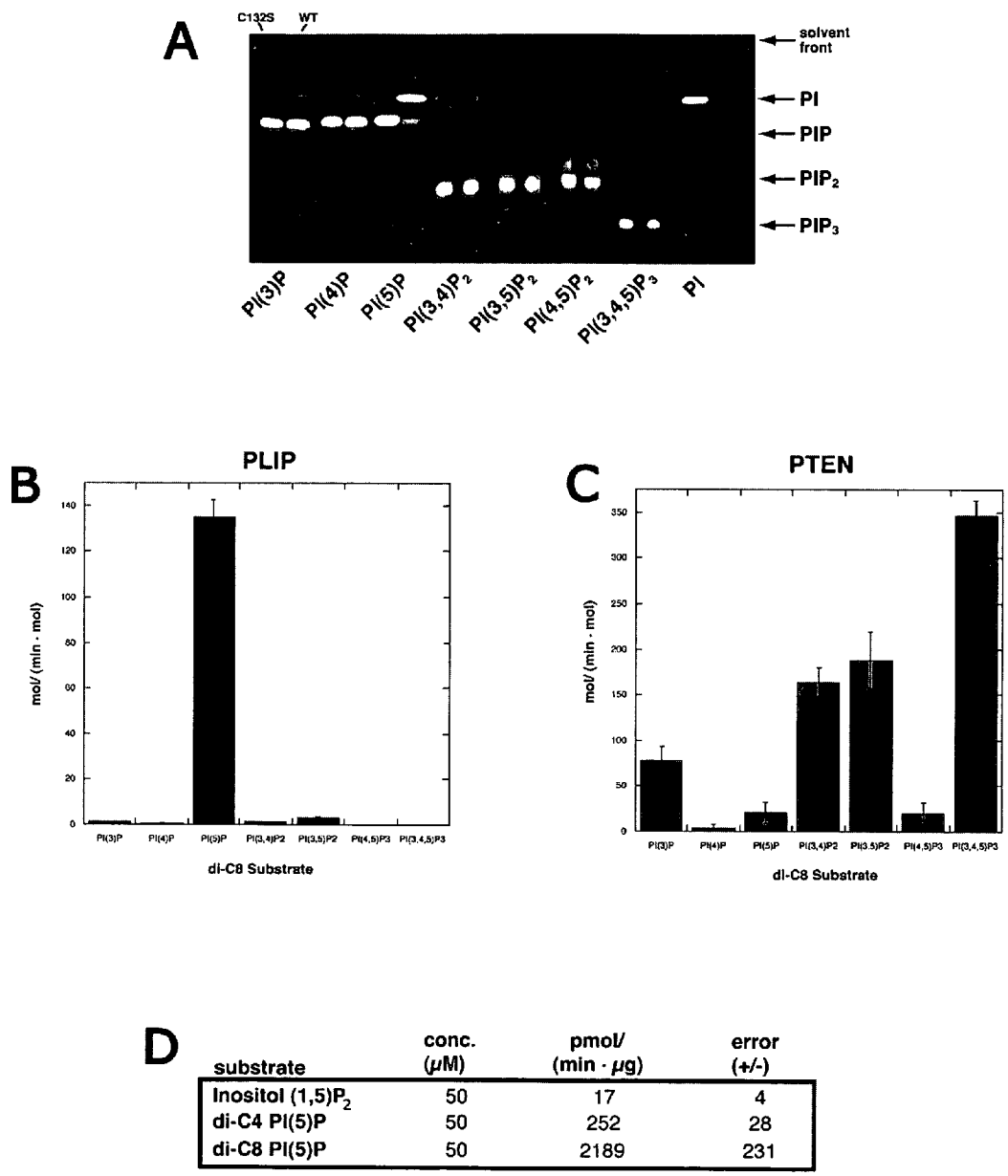
FIG. 2 illustrates the analysis of PLIP activity against phosphoinositides. In A wild-type (WT) or catalytically inactive (C132S) PLIP was tested against a panel of water-soluble BODIPY-tagged di-C6 phosphoinositides. B and C show the activity of PLIP or PTEN against di-C8 PIs incorporated into a lipid bilayer with phosphatidylserine carrier lipid. D shows the activity of PLIP against water soluble PI(5)P derivatives of varying acyl chain length.

A pH/rate profile for PLIP performed with various substrates revealed this enzyme to be most efficient at pH 5.5. Therefore, all further assays were performed at this pH. Since PLIP had active site residues similar to those found in PTEN, Applicants examined its activity toward a panel of fluorescently-labeled di-$C_6$ phosphoinositides. A TLC analysis of the reaction products, shown in FIG. 2A, revealed that PLIP exhibits a highly selective substrate specificity for PI(5)P. FIG. 2 illustrates the analysis of PLIP activity against phosphoinositides. In Figure A wild-type (WT) or catalytically inactive (C132S) PLIP was tested against a panel of water-soluble BODIPY-tagged di-C6 phosphoinositides. Conversion of PI(5)P to PI by wild-type PLIP is indicated with a red arrow. Migration distances of the various PI derivatives are indicated on the right.

This substrate preference is shared by the *Dictyostelium* ortholog of PLIP (Merlot et al., 2003). As expected, mutation of the predicted catalytic cysteine residue to serine (C132S) nullified this activity. To further confirm this result, PLIP was tested against a panel of di-$C_8$ PI's presented in a lipid bilayer with phosphatidylserine carrier lipid. PLIP again demonstrated robust activity against PI(5)P—44-fold greater than against PI(3,5)$P_2$, its second most preferred substrate (FIG. 2B). This is a notable enhancement in specificity compared with PTEN which exhibits only a 1.8-fold preference for PI(3,4,5)$P_3$ over PI(3,5)$P_2$ (FIGS. 2B, 2C). PLIP assayed against di-$C_{16}$ PI's revealed highly similar results. FIGS. 2B and 2C show the activity of PLIP or PTEN against di-C8 PIs incorporated into a lipid bilayer with phosphatidylserine carrier lipid.

Applicants also tested water soluble PI(5)P of multiple acyl chain lengths as substrates for PLIP, as this variable has been shown to affect the level of enzymatic activity for other PI phosphatases (Mochizuki and Majerus, 2003; Taylor et al., 2000). PLIP demonstrated a 10-fold increase in activity against di-$C_4$ PI(5)P versus the inositol head group, inositol (1,5)P$_2$, and a second 10-fold increase against di-C$_8$ PI(5)P versus di-C$_4$ PI(5)P (FIG. 2D), suggesting that this lipid moiety is also an important factor for PLIP activity. FIG. 2D shows the activity of PLIP against water soluble PI(5)P derivatives of varying acyl chain length.

PI(5)P Activity is Not a General Feature of PTP's

Due to the only recent emergence of PI(5)P as a known signaling molecule, few PTP's have been tested for activity against this substrate. To ensure that activity against PI(5)P is not a common feature of PTP's, membrane-bound di-C$_8$ PI(5)P was assayed using a known tyrosine-specific PTP (TC-PTP) and a known dual-specific PTP (VHR) (Ishibashi et al., 1992; Zhao et al., 1992; Ruzzene et al., 1993; Zhou et al., 1994; Denu et al., 1995). Both enzymes yielded activity that was barely detectable above background, indicating that PI(5)P activity is not a general feature of the various classes of PTP's (Table 1). PTEN and MTM1, known PI phosphatases, both possess the ability to dephosphorylate PI(5)P, however with 17- and 200-fold less efficiency than toward their preferred substrates, respectively.

PLIP Exhibits Poor Protein Phosphatase Activity

A characteristic of all PI phosphatases to date has been their extremely poor activity toward proteinaceous substrates (Taylor et al., 2000). To determine if PLIP is consistent with this trend, its activity was measured against radiolabeled myelin basic protein and casein side-by-side with the aforementioned phosphatases. PLIP's activity against these substrates was very poor, most closely resembling that of PTEN and myotubularin, and was approximately 1000-fold lower than PLIP's activity against PI(5)P (Table 1).

TABLE 1

Phosphatase activity of various PTPs
Activity measurements are reported in mole
of phosphate released/min/mol of enzyme.
All measurements were performed in triplicate.
S.E. was less than 5% in all cases.

|  | TC-PTP | VHR | PLIP | PTEN | MTM1 |
|---|---|---|---|---|---|
|  |  |  | mol/(min mol) |  |  |
| PI (3) P | ND$^a$ | ND | 1.3$^b$ | 77.9$^b$ | 4470$^d$ |
| PI (5) P | ~0.0$^b$ | ~0.0$^b$ | 135$^b$ | 20.4$^b$ | 22.7$^d$ |
| PI (3, 4, 5) P3 | ND | ND | 3.1$^b$ | 346$^b$ | 2.1$^d$ |
| MyBP Tyr(P) | 195$^b$ | 0.5$^b$ | 0.1$^b$ | ~0.0$^c$ | ~0.0$^d$ |
| Casein Ser(P) | 1440$^b$ | 1.8$^b$ | 0.2$^b$ | ~0.0$^c$ | 0.1$^d$ |
| MyBP Ser(P)/Tyr(P) | ~0.0$^b$ | ~0.0$^b$ | ~0.0$^b$ | ~0.0$^c$ | ~0.0$^d$ |
| Casein Ser(P) | ~0.0$^b$ | ~0.0$^b$ | ~0.0$^b$ | ~0.0$^c$ | ~0.0$^d$ |

$^a$ND, not determined.
$^b$This study.
$^c$Ref. 43.
$^d$Ref. 32.

Figure 3:
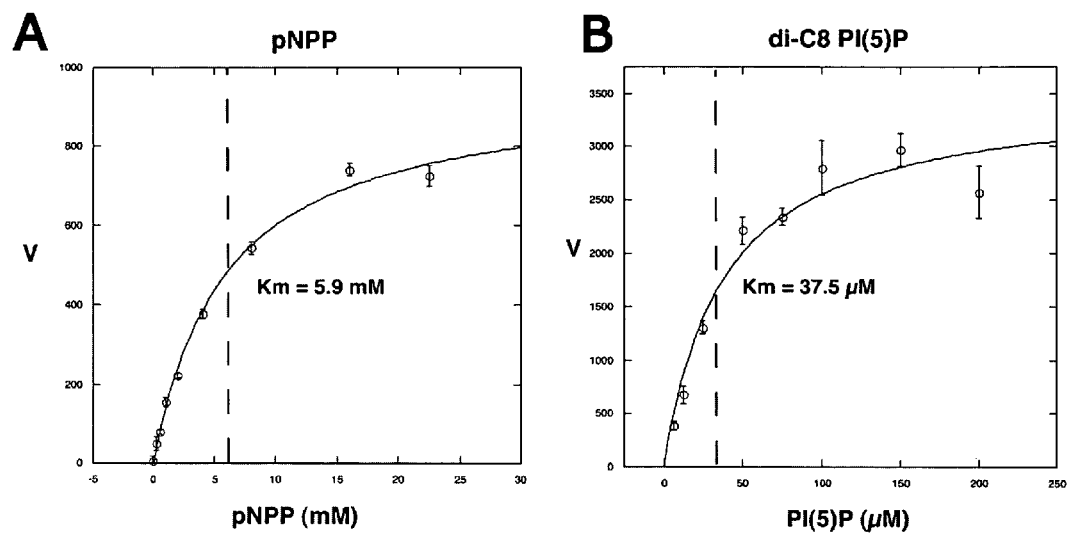
FIG. 3 illustrates the kinetic analysis of PLIP phosphatase activity. Saturation kinetics for PLIP against pNPP (A) and water-soluble di-C8 PI(5)P (B) are shown.

To further explore PLIP's propensity to act as a protein phosphatase, a kinetic analysis of its activity toward the artificial phosphotyrosine analog, para-nitrophenyl phosphate (pNPP), alongside with di-C8 PI(5)P were performed (Taylor et al., 1997). FIG. 3 illustrates the kinetic analysis of PLIP phosphatase activity. Saturation kinetics for PLIP against pNPP (A) and water-soluble di-C8 PI(5)P (B) are shown. V (reaction velocity) is in units of pmol/(min µg). PLIP demonstrated a Km of 5.9 mM against this substrate, more than 150-fold higher than the Km of 37.5 µM seen for di-C$_8$ PI(5)P.

Thus, PLIP demonstrated a clear preference for PI(5)P over any other proteinaceous or lipid substrate tested. Although efforts to demonstrate PLIP's effect on endogenous PI(5)P levels are ongoing, Applicants note that in vitro observations have often served as indicators of in vivo function for PI phosphatases (Niebuhr et al., 2002; Terebiznik et al., 2002; Maehama and Dixon, 1998; Tronchere et al., 2003).

PLIP is a Testis-Enriched Phosphatase

Figure 4:
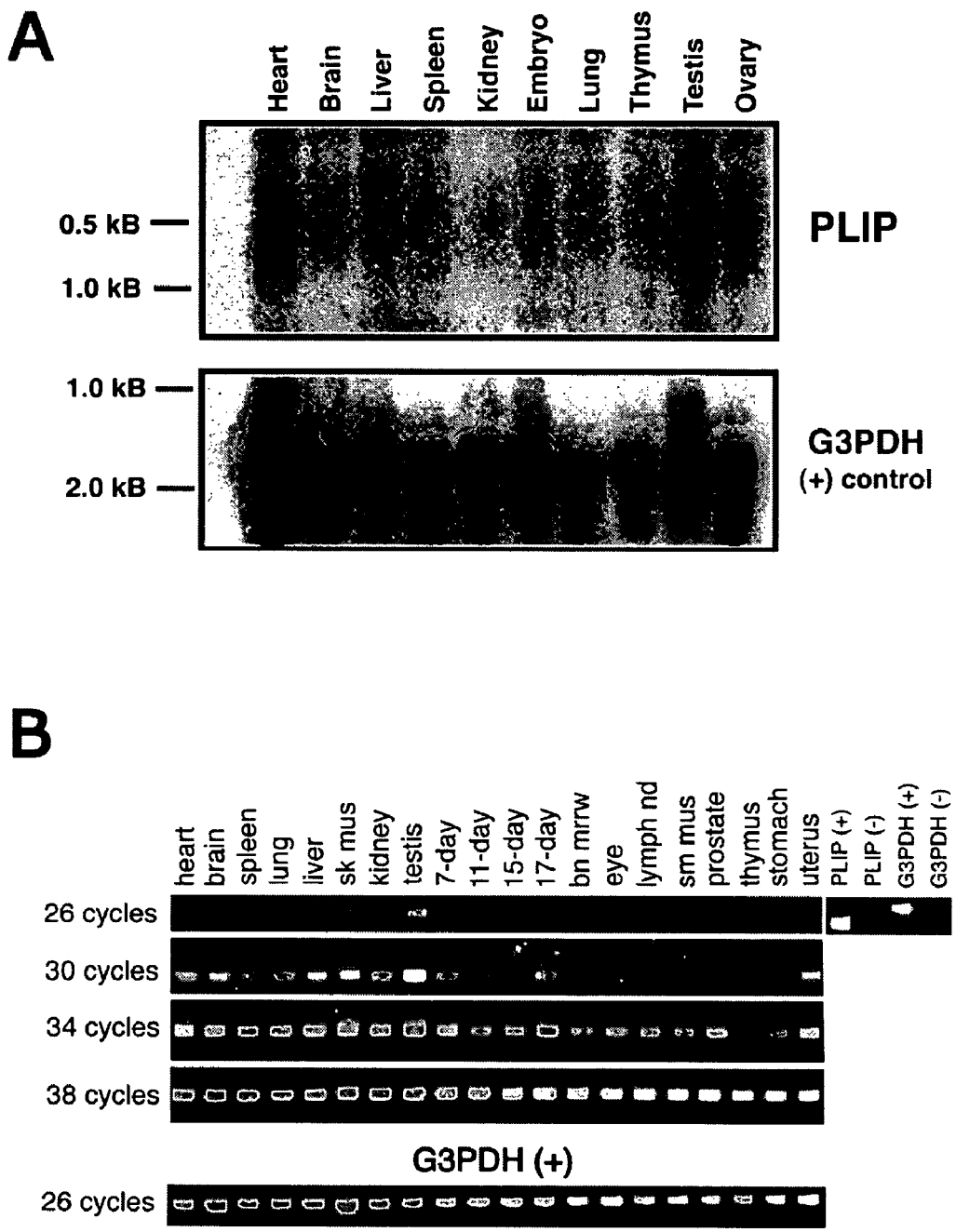
FIG. 4 illustrates a PLIP mRNA expression profile. A shows the Northern blot analysis of PLIP mRNA levels in various murine tissues. B shows the PCR analysis of cDNA derived from reverse-transcribed mRNA from various murine tissues.

The relative tissue distribution of PLIP was determined by a Northern blot assay using a $^{32}$P-labelled, random-primed PLIP cDNA probe. FIG. 4 illustrates a PLIP mRNA expression profile. A shows the Northern blot analysis of PLIP mRNA levels in various murine tissues. B shows the PCR analysis of cDNA derived from reverse-transcribed mRNA from various murine tissues. Positive controls for PLIP and glyceraldehyde-3-phosphate dehydrogenase (G3PDH) were performed using cloned DNA sequences for each protein. Negative control lanes represent reactions performed without the addition of template DNA. A major band was detected in the testis lane consistent with the predicted size of the PLIP transcript (FIG. 4A). Glyceraldehyde-3-phosphate dehydrogenase (G3PDH), probed as a positive control, showed strong expression in all tissues. This result was confirmed by a highly sensitive PCR analysis of cDNA from various tissue lysates which detected PLIP in testis after 26 cycles (FIG. 4B). Relatively high amounts of PLIP cDNA could also be detected in brain, liver, skeletal muscle, and uterus. After 38 PCR cycles, all lanes were positive, indicating that a small amount of message is present in all tissues tested (FIG. 4). The relative enhancement of PLIP in testis tissue is interesting as it follows similar results for two other new PTEN-like phosphatases, PTEN2 and TPIP (Walker et al., 2001; Wu et al., 2001).

PLIP is Not a Regulator of Akt Activation

Recently, Carricaburu, et. al., proposed that PI(5)P may control Akt activation by regulating the activity of a PI(3,4,5)P$_3$ phosphatase (Carricaburu et al., 2003). In their study, they report that depletion of intracellular PI(5)P by a PI(5)P kinase results in abbreviation of Akt activation (FIG. 5A). To test whether PLIP could modulate Akt activity, Applicants overexpressed, catalytically inactive C132S PLIP, or vector control along with FLAG-tagged Akt into CHO-IR cells. After serum-starvation and ±insulin treatment (see Experimental Procedures), Akt was immunoprecipitated and analyzed by western blotting. Full activation of Akt requires that it is phosphorylated on serine 473 on its carboxy terminus. As seen in FIG. 5, the level of Akt phosphorylation on serine 473 is not significantly affected by overexpression of WT or C132S PLIP, with or without insulin treatment. To ensure that this result was not due to an artifact of overexpression, Applicants used RNAi to knock down the mRNA levels of PLIP in Drosophila S2 cells, which have previously been shown to possess the members of the Drosophila Akt signaling pathway (Clemens et al., 2000; Weinkove et al., 1997; Lizcano et al., 2003). S2 cells were treated with buffer (negative control), PLIP, or PTEN dsRNA, followed by Akt immunoprecipitation and activity assays. Despite a major reduction in mRNA levels, Akt activity was unaffected by PLIP RNAi treatment, whereas the PTEN knockout exhibited the previously reported enhancement of Akt activity (FIG. 5) (Clemens et al., 2000). From these data, it was conclude that PLIP is not a modulator of Akt function. Furthermore, unless PLIP, despite being overexpressed, is not spatially poised to alter the necessary PI(5)P pools in vivo, these data weaken the idea that this lipid is capable of regulating Akt activity.

The characterization of PLIP as a highly specific PI(5)P phosphatase is a potentially important contribution to our understanding of PI regulation, and adds a powerful tool for further analysis of PI signaling pathways within the cell. Until a clear demonstration of PLIP's ability to alter PI(5)P levels in vivo is achieved, however, the possibility that it possesses a distinct endogenous substrate not assessed in this study, cannot be ruled out. Even if PLIP utilizes a highly specific proteinaceous substrate in vivo, the fact that it possesses this unique and well-characterized preference for PI(5)P should make it possible to selectively measure PLIP activity under a variety of experimental conditions. Detailed investigations into the subcellular localization, in vivo enzymatic activity, and overall cellular function of PLIP are ongoing in our laboratory.

FIG. 5 illustrates the analysis of PLIP as an effector of Akt activity. A shows a proposed model of PI(5)P regulation of Akt activity, adapted from Carricaburu et al. (20). In B wild-type (WT) PLIP, catalytically inactive (C132S) PLIP, or vector control were transfected along with FLAG Akt into Chinese hamster ovary-insulin receptor cells and treated with (+) or without (−) insulin. Following immunoprecipitation with anti-FLAG-agarose beads, Akt and phospho-Akt levels were probed via Western blot using anti-FLAG and anti phospho-serine 473-Akt-specific antibodies, respectively. A third blot was performed on the cell lysates using anti-V5 (PLIP) to demonstrate the presence of wild-type and C132S PLIP. Note that because of a relatively higher level of Akt expression in the vector control cells, lanes 1 and 2 are derived from lower film exposure times. Results are representative of two separate experiments. In C) *Drosophila* S2 cells were treated with buffer (U) or PLIP or PTEN dsRNA. Following treatment, endogenous Akt was immunoprecipitated and assayed for activity. The effectiveness of the dsRNA treatment, as assessed by mRNA levels, is shown in the blot below.

Example 2

Materials and Methods

Cloning and Plasmid Construction

Mouse PTPMT1 and PTPMT1 truncation mutants were cloned into pcDNA3.1D/V5-His-TOPO using a TOPO cloning kit (Invitrogen). The first 37 amino acids of PTPMT1 were excised from the full-length construct by restriction digest with Kpn I (New England Biolabs), and ligated into pEGFP-N2 (Clontech). Adenoviral vectors containing a U6 promoter for the production of shRNAs directed against PLIP were constructed using the BLOCK-iT RNAi expression system (Invitrogen). The following sequences were used as the shRNAs:

Cell Culture, Transfection, and Immunocytochemistry (ICC)

COS-1 cells were maintained at 37° C. and 5% $CO_2$ in DMEM (Invitrogen) containing 10% FBS, 50 U/ml each of penicillin and streptomycin, and 4 mM glutamine. Cells were transfected using Fugene (Roche), following the manufacturer's recommended protocol. For ICC, cells were incubated at 37° C. with 100 nM of MitoTracker Red (Molecular Probes) in DMEM for 30 minutes before fixation with 3.7% formaldehyde and permeabilization with cold acetone. Cells were incubated with anti-V5 tag monoclonal antibody (Invitrogen) at 1:500 in 0.1% BSA in PBS, and anti-mouse FITC conjugated secondary antibody at 1:100 (Vector Laboratories) before viewing.

Generation of PTPMT1 Polyclonal Antibodies

Full length GST-tagged mouse PTPMT1 (expressed and purified as described (Pagliarini et al., 2004)) was used to raise antisera in rabbits (Cocalico). Serum was run sequentially over a GST column to remove any GST antibodies, and a GST-PTPMT1 column to affinity purify PTPMT1 antibodies (Harlow and Lane, 1988).

Purification of Rat Liver Mitochondria

Mitochondria were purified as described (Lapidus and Sokolove, 1993), with minor modifications. Fresh rat liver was minced, washed and resuspended with ~5 volumes of MSHE (210 mM mannitol, 70 mM sucrose, 5 mM HEPES (pH'd with KOH to 7.4), 1 mM EGTA, 0.5% fatty acid-free BSA and protease inhibitor cocktail (Roche)). Livers were homogenized with 30-40 strokes of a tight-fitting homogenizer attached to a drill press at full speed. Homogenate was spun at 2300 rpm for 10 minutes in a Sorvall SS-34 rotor to pellet nuclei and unbroken cells. This pellet was rehomogenized and respun at 2300 rpm. The supernatants were combined and spun at 11,200 rpm for 10 minutes to pellet the crude mitochondrial fraction. Mitochondria were washed in BSA-free MSHE, repelleted, and again resuspended in a small volume (~1-2 ml) of BSA-free MSHE. Mitochondria were then placed on top of a gradient of 35% histodenz (Sigma), 17.5% histodenz, and 6% Percoll and spun at 19,000 rpm in an SW40 Ti rotor (Beckman) for 45-60 minutes. Mitochondria were collected from the 35% and 17.5% histodenz interface, washed with MSHE, repelleted at 11,200 rpm, and either used immediately or snap frozen in liquid nitrogen and stored at −80° C. until use. Mitochondria from 100-150 15 cm dishes of INS-1 832/13 cells were purified by the same protocol.

Immunogold Electron Microscopy

Rat liver was perfusion fixed with 4% PFA in 0.1 M phosphate buffer and then fixed overnight in 8% PFA in phosphate buffer. Samples were rinsed with 0.15% glycine in 0.1 M phosphate buffer, pelleted in 10% gelatin (Knox) in phosphate buffer and cryoprotected by infusion with 2.3 M sucrose/phosphate buffer overnight at 4° C. 1 $mm^3$ tissue blocks were mounted onto specimen holders and snap frozen in liquid nitrogen. 70-90 nm ultrathin cryosections were cut at −100° C. on a Leica Ultracut UCT with EM FCS cryoattachment using a Diatome diamond knife, picked up with a 1:1 mixture of 2.3 M sucrose and 2% methyl cellulose (15 cp) as described (Liou et al., 1996), and transferred onto Formvar and carbon-coated copper grids. Immunolabeling was performed by slight modifications of the "Tokuyasu technique" (Tokuyasu, 1980), using anti-PTPMT1 and anti-COX at 1:100, and gold conjugated goat anti-rabbit IgG and gold conjugated goat anti-mouse IgG (Amersham Pharmacia Biotech) at 1:25.

Mitochondrial Subfractionation

Separation of inner and outer mitochondrial membranes was performed as described (Felgner et al., 1979; Sottocasa et al., 1967). Purified rat liver mitochondria were resuspended in hypotonic medium (10 mM KCl, 2 mM HEPES, pH 7.2) at 10 mg/ml with gentle stirring for 20 minutes on ice. One-third volume of hypertonic medium (1.8 mM sucrose, 2 mM ATP, 2 mM $MgSO_4$, 2 mM HEPES, pH 7.2) was then added and the solution stirred for an additional 5 minutes. The mitochondria were sonicated for 15 seconds at 3 amps before being layered on top of a stepwise gradient of 0.76, 1.0, 1.32, and 1.8 M sucrose and spun at 25,000 rpm for 3 hrs. in an SW40 Ti rotor. The soluble inter-membrane space (IMS) fraction was collected from the upper supernatant, the outer membrane (OM) from between the 0.76 and 1.0 M interface, and the mitoplasts (MP) from the pellet. The MP and OM fractions were washed with MSHE and repelleted (MP @10,000×g for 10 minutes, OM @120,000×g for 45 minutes). Submitochondrial particles (SMP) were generated as described (Lesnefsky et al., 2001). Mitochondria were resuspended at 10-15 mg/ml and sonicated 3×2 minutes on ice with one-minute intervals.

Solution will turn from cloudy to transparent. The solution was spun at 10,000×g for 10 minutes to pellet unbroken mitochondria, and the resulting supernatant at 120,000×g for 45 minutes to pellet SMPs. Supernatant was saved as the matrix/inter-membrane space fraction (M). SMP pellet was washed once with MSHE and repelleted.

Immunohistochemistry

IHC of mouse pancreas paraffin sections was performed with minor modifications as described (Hogan et al., 1994), with the anti-PTPMT1 antibody or preimmune serum used at 1:200.

ATP and ADP Assays

PTPMT1 expression in INS-1 832/13 cells was knocked down using 200 pmol of Ambion siRNA (sense: 5'-GUCU-GUGGAUGACAAAGAAtt-3' (SEQ ID NO:3), antisense: UUCUUUGUCAUCCACAGACtt-3' (SEQ ID NO:4)) in an Amaxa nucleoporator with buffer T on program T-20, according to the manufacturer's protocol. Approximately 72 hrs post siRNA treatment, cells were treated as outlined in the text, pelleted and lysed in 2% TCA via sonication and/or vortexing. Precipitates were pelleted at 13,200 rpm for 2 minutes. The supernatant was removed, neutralized with 0.5 M Tris pH 7.4, and analyzed for ATP using Promega's ENLITEN luciferase bioluminescence reagent at an appropriate dilution. All ATP measurements were normalized to protein levels, as measured by the BCA method (Pierce). ADP levels were determined by converting ADP to ATP with pyruvate kinase, remeasuring ATP by the above assay, and subtracting the initial ATP readings, as reported (Gorman et al., 2003).

Glucose-Stimulated Insulin Secretion Assays

INS-1 832/13 cells ($5 \times 10^6$ per reaction) were electroporated as above, and split between 4 wells of a 12-well plate. After 72 hours, cells were washed once with low glucose (3 mM) standard assay buffer (SAB: 114 mM NaCl, 4.7 mM KCl, 1.2 mM $KH_2PO_4$, 1.16 mM $MgSO_4$, 20 mM HEPES pH 7.2, 25.5 mM $NaHCO_3$, 10 mM $CaCl_2$, 0.2% BSA), and then preincubated for 2 hours in fresh low glucose SAB. After preincubation, 1 mL of low or high (15 mM) glucose SAB was added to each well. At the end of the incubation time, the SAB was removed and saved, and the cells were washed once in PBS, and lysed by freezing and thawing in a Tris-EDTA solution (20 mM Tris pH 7.4, 20 mM EDTA pH 8.0, 10 mM DTT, protease inhibitors). A Bio-Rad protein assay was performed on each lysate sample to standardize the insulin assay results for protein. The $^{125}$I-insulin Coat-A-Count RIA (Diagnostic Products Corp.) was used to assay SAB samples for insulin content.

Analysis of Phosphoinositides and Phosphoproteins from INS-1 831/13 Mitochondria Mitochondrial lipids from 100 μg of either control or PTPMT1 knockdown cells were extracted via the Bligh-Dyer method, and PI(4)P and PI(5)P levels were analyzed using PIPKIα and PIPKIIβ (constructs kindly provided by Dr. Lucia Rameh), as described (Morris et al., 2000). For phosphoprotein analysis, control and PTPMT1 knockdown mitochondria were resuspended to a concentration of 1 μg/μl, briefly sonicated to disrupt the membranes, and treated±calf intestinal phosphatase (CIP-New England Biolabs) for 1 h at 37° C. Ten μg of each sample were then analyzed by immunoblot for phosphoproteins using a panel of phospho-specific antibodies from Cell Signaling Technology (CST), according the manufacturers protocol.

Results and Discussion

Applicants initially cloned the uncharacterized dual-specific protein tyrosine phosphatase (DS-PTP) PTPMT1 due to the similarity of its active site to that of the tumor suppressor phosphatase PTEN (Pagliarini et al., 2004)*. FIG. 6A shows the primary sequence alignment of the active site region of mouse PTPMT1 and PTEN using the Clustal W algorithm. Amino acid similarities are shaded in light gray, identities in dark gray. Active site basic residues are outlined in dark blue.

We previously referred to this phosphatase as PLIP (PTEN-Like Phosphatase), but have altered the name per request of the Mouse Genome Nomenclature Committee due to the current usage of the acronym PTPMT1 for the cPLA(2)-interacting Protein PTPMT1 has also been referred to as MOSP in a recent review article (Alonso et al., 2004).

PTPMT1 is a Mitochondrial Phosphatase

To analyze the subcellular location of PTPMT1, Applicants cloned the open reading frame encoding the mouse protein into a C-terminal V5-tagged mammalian expression vector and transiently transfected COS-1 cells. Cells were visualized by immunofluorescence 24 hours post transfection, along with the mitochondrial marker, MitoTracker Red. Immunocytochemistry (ICC) revealed a staining pattern that overlapped with the mitochondrial marker, MitoTracker Red (FIG. 6B). This localization was unexpected, as none of the 107 PTPs have been localized to this organelle (Alonso et al., 2004). FIG. 6B shows the PTPMT1 localization to the mitochondria. Yellow color in the third panel depicts colocalization.

Given the novelty of this observation, it was imperative to rigorously establish PTPMT1 as a bona fide mitochondrial phosphatase. To ensure that the observed mitochondrial staining was not due to an artifact of overexpression, location of endogenous PTPMT1 was analyzed. Mitochondria from rat liver, a tissue previously shown to possess high levels of PTPMT1 mRNA (Pagliarini et al., 2004), were purified by differential and density gradient centrifugation. Immunoblot analysis of each fraction demonstrated this approach to yield highly pure mitochondria (Cytochrome c marker) that was free of endoplasmic reticulum (KDEL marker). FIG. 6C shows SDS-PAGE and immunoblot analysis of twenty μg of rat liver whole cell lysate (WCL), differential centrifugation purified mitochondria (DC), and metrizamide gradient purified mitochondria (MTZ) using KDEL antibody for ER, cytochrome c antibody for mitochondria, and anti-PTPMT1 antibody. This subsequent anti-PTPMT1 immunoblot using an affinity purified polyclonal antibody generated against recombinant mouse protein revealed PTPMT1 to copurify with cytochrome c, indicating that endogenous PTPMT1 resides either inside or on the outer membrane of mitochondria.

PTPMT1 is Targeted to the Mitochondria by an N-Terminal Signal Sequence

Figure 7:
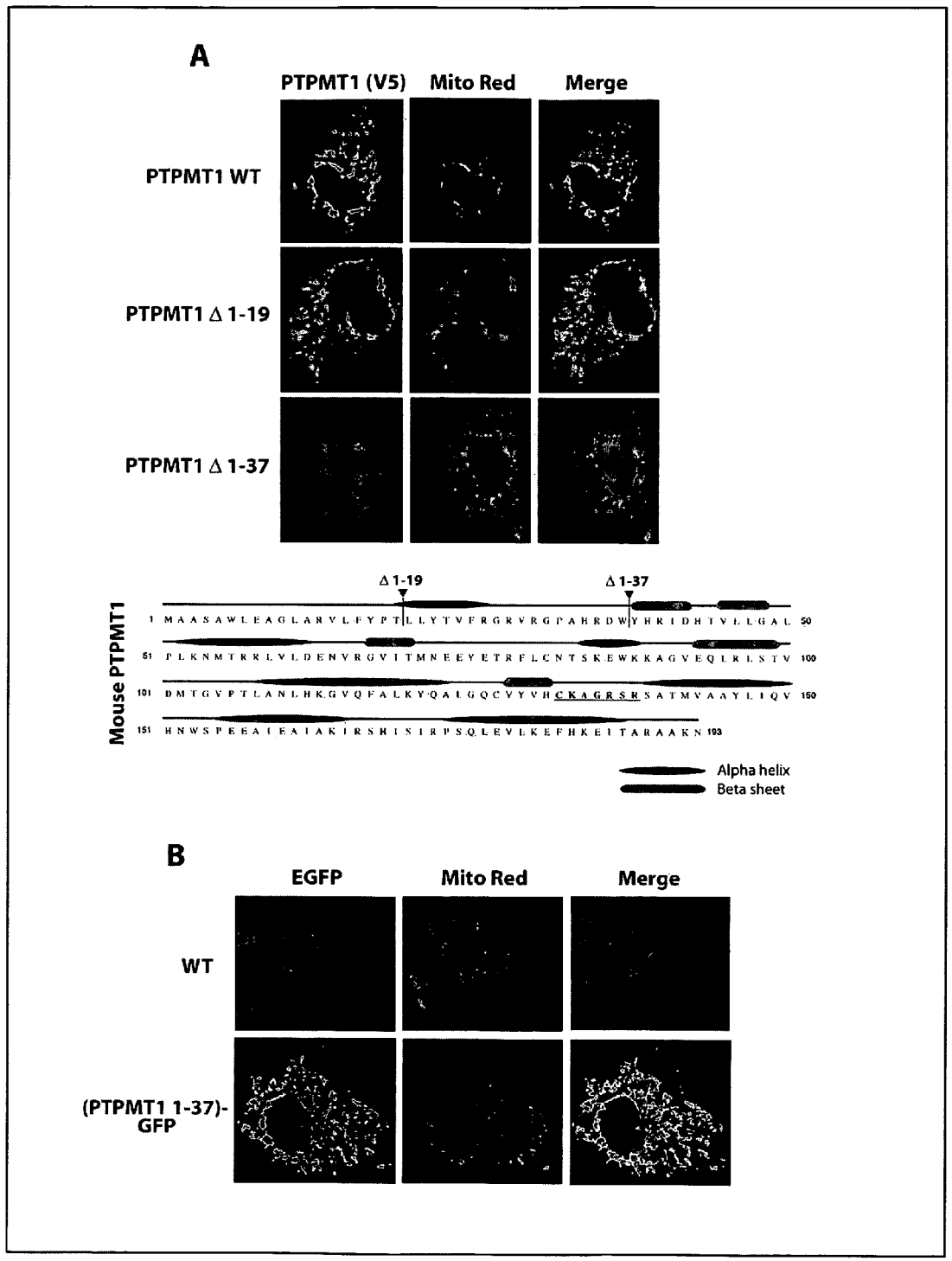
FIG. 7 illustrates that an N-terminal signal sequence directs PTPMT1 to mitochondria (SEQ ID NO:40). A shows COS-1 cells expressing C-terminal V5-tagged wild type (WT), Δ1-19, or Δ1-37 mouse PTPMT1 after incubation with MitoTracker Red 24 hours after transfection and analysis for fluorescence using a FITC conjugated anti-mouse secondary antibody. The PTPMT1 primary sequence below indicates the sites of truncation. The PTPMT1 active site is underlined with its catalytic residues in red. B shows COS-1 cells expressing wild type EGFP or EGFP possessing the first 37 amino acids of PTPMT1 on its N-terminus after incubation with MitoTracker Red and visualized as above.

Ninety-nine percent of mitochondrial proteins are nuclearly encoded, and therefore must be translocated into the mitochondria from the cytosol. Proteins destined for the matrix or inner membrane are often translated as preproteins possessing a loosely-defined N-terminal presequence that is recognized by the mitochondrial translocase of the outer membrane (TOM) complex (Rehling et al., 2004). This presequence often includes an alpha helix and multiple basic residues. The N-terminal region of PTPMT1 includes four highly conserved basic residues and a predicted alpha helix typical of PTPs (FIG. 7A). To test if the N-terminus of PTPMT1 possesses the necessary elements to direct mitochondrial localization, two N-terminal truncations were made: Δ1-19, which does not include the predicted alpha helix, and Δ1-37, which deletes the entire N-terminus preceding the first β-sheet of the PTP fold (FIG. 7A). Wild type PTPMT1 and both mutants, each with a C-terminal V5 tag, were transfected into COS-1 cells. Subsequent ICC demonstrated PTPMT1's mitochondrial localization to be unaffected by the Δ1-19 truncation, but completely abolished by the Δ1-37 truncation (FIG. 7A). A more conclusive demonstration of the ability of PTPMT1's N-terminus to direct mitochondrial localization was seen by fusing the first 37 amino acids to the N-terminus of enhanced green fluorescent protein (EGFP). This addition caused the normally cytoplasmic/nuclear EGFP to be completely redirected to the mitochondria, as assessed by its colocalization with MitoTracker Red (FIG. 7B). Together, these data demonstrate the N-terminal region of PTPMT1 to be both necessary and sufficient to direct mitochondrial localization.

Endogenous PTPMT1 Resides on the Inner Mitochondrial Membrane

FIG. 8 shows that PTPMT1 is tightly associated with the matrix face of the inner mitochondrial membrane. A shows Immunogold EM staining of rat liver sections. 1 and 2, sections probed with anti-PTPMT1 primary and anti-rabbit 10 nM gold conjugated secondary antibodies at 21,000× and 28,000× magnification, respectively. 3, same as 1 co-stained with anti-cytochrome oxidase primary and anti-mouse 5 nM gold conjugated secondary antibody. 4, same as 1 without primary antibody as negative control. B is a cartoon summary of mitochondrial subfractionation strategy. In C fifteen µg of each submitochondrial fraction (see text) were separated by SDS-PAGE and immunoblotted for markers to each fraction (ANT-adenine nucleotide transporter, VDAC-voltage dependant anion channel, GRP 75-glucose regulated protein). In D three-hundred and fifty µg of MPs or SMPs were incubated with 2.5 µg of trypsin protease in 100 µl buffer for the indicated times at room temperature, pelleted, and analyzed by immunoblotting for PTPMT1. Immunoblots for the matrix marker GRP-75 were performed to demonstrate the integrity (MP) and disruption (SMP) of the IM. In E whole mitochondria were treated with increasing amounts of digitonin to sequentially disrupt the outer and inner mitochondrial membranes. Following treatment, mitochondria were washed with either high salt, or high pH (11.5) buffer, repelleted, and immunoblotted for the indicated protein. A blot for the matrix chaperone GRP-75 was performed to demonstrate the disruption of the inner mitochondrial membrane at ≧1.0 µg/µl digitonin.

Figure 8A:
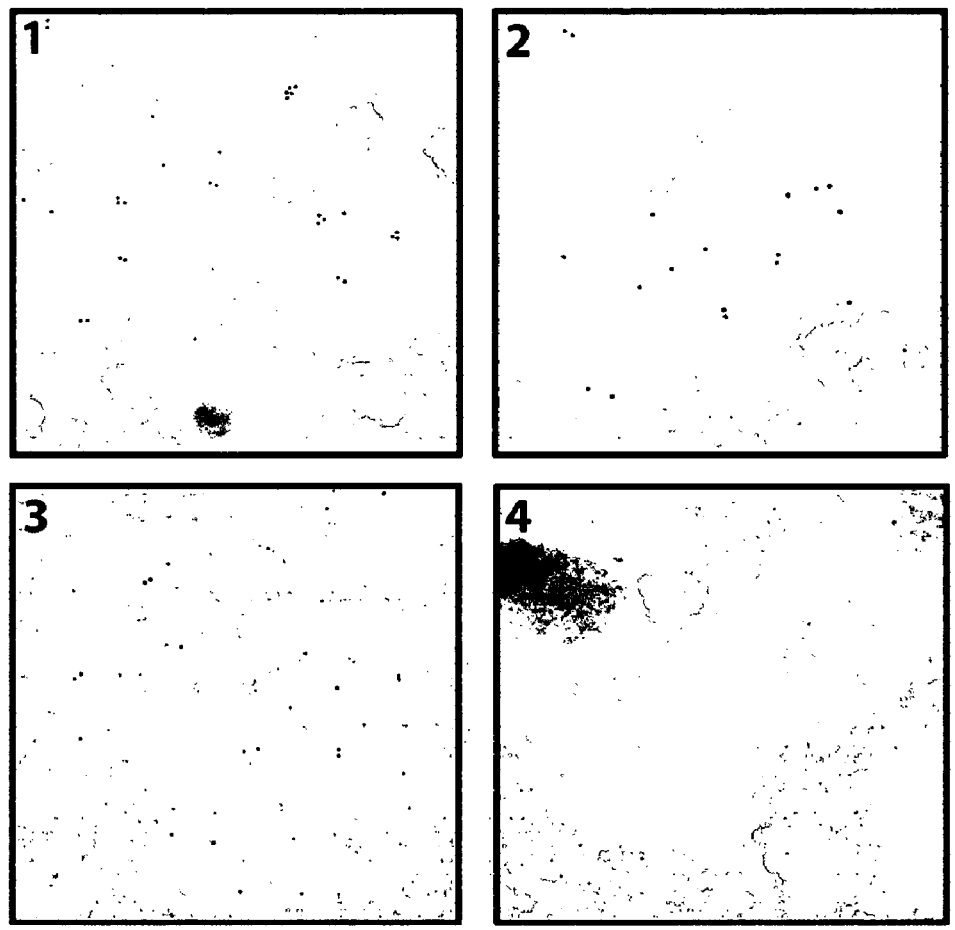
FIG. 8 shows that PTPMT1 is tightly associated with the matrix face of the inner mitochondrial membrane. A shows Immunogold EM staining of rat liver sections. B is a cartoon summary of mitochondrial subfractionation strategy. C shows the submitochondrial fractions after SDS-PAGE and immunoblotted for markers to each fraction. In D MPs or SMPs were incubated with trypsin, pelleted, and analyzed by immunoblotting for PTPMT1. Immunoblots for the matrix marker GRP-75 were performed to demonstrate the integrity (MP) and disruption (SMP) of the IM. E shows that whole mitochondria treated with increasing amounts of digitonin to sequentially disrupt the outer and inner mitochondrial membranes.

To further define PTPMT1's localization within the mitochondrion immunogold EM staining was performed. Ultrathin cryosections of whole rat liver were probed with an affinity-purified anti-PTPMT1 primary antibody and a 10 nm gold particle-conjugated goat anti-rabbit secondary antibody. Positive staining was seen in most mitochondria with little background staining of other subcellular compartments (FIG. 8A). PTPMT1's staining pattern closely matched that of the inner mitochondrial membrane marker cytochrome c oxidase (COX), with nearly all of the PTPMT1 staining seen along the cristae. No background staining was seen with secondary antibody alone (FIG. 8A).

Figure 8B:
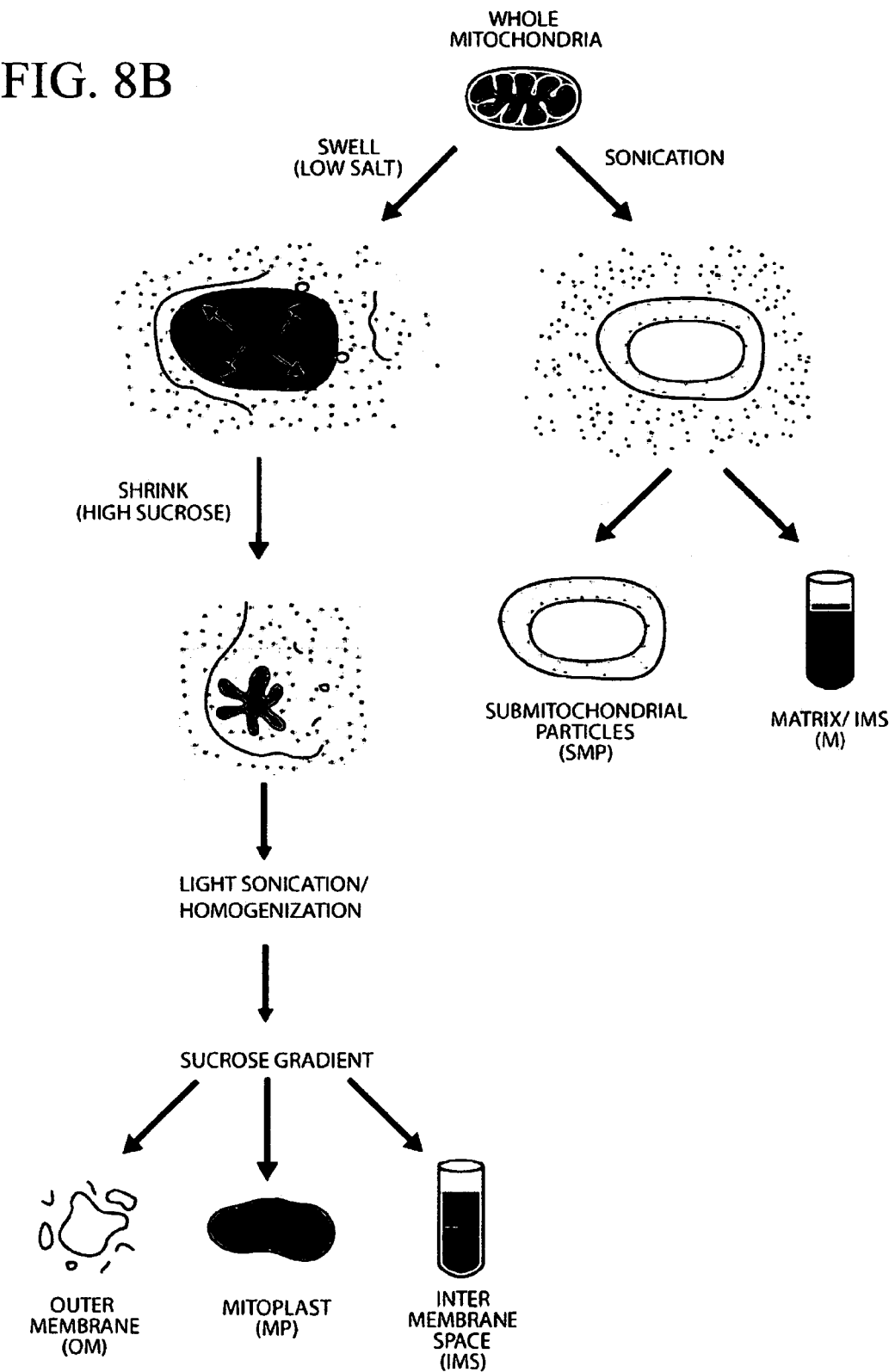
Figure 8C:
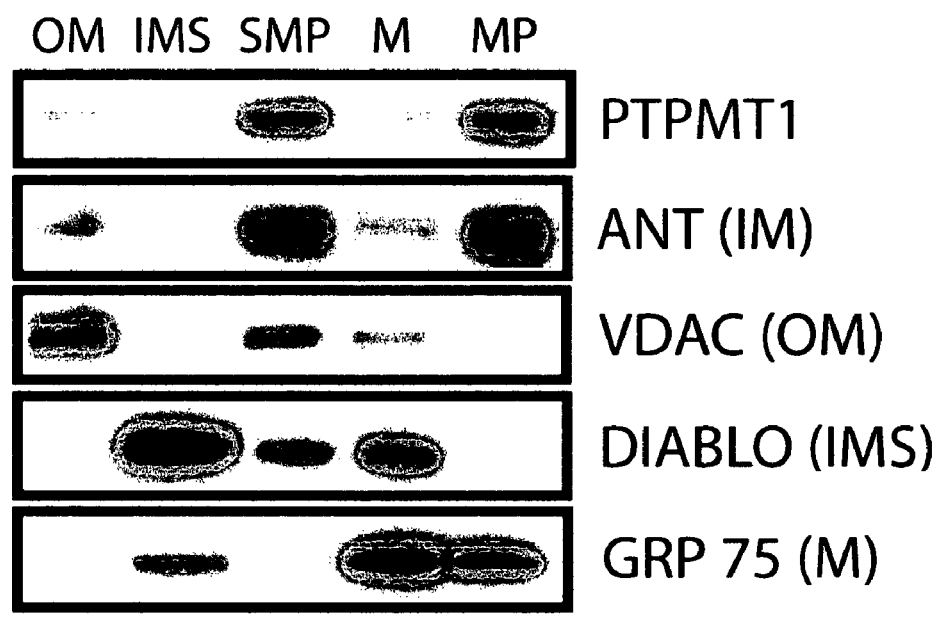

The EM results suggested that PTPMT1 resides within mitochondria, as opposed to interacting with the mitochondrial outer membrane. To further define PTPMT1's submitochondrial location, rat liver mitochondria was separated into the following fractions: outer membrane (OM), mitoplasts (MP—inner membrane and matrix), inter-membrane space (IMS—soluble material between the inner and outer membranes), sub-mitochondrial particles (SMP—inside-out mitochondrial membranes devoid of most soluble material), and Matrix/IMS (M—soluble material from within the inner membrane and most inter-membrane space) (FIG. 8B and see Experimental Procedures). To demonstrate successful separation, each fraction was immunoblotted with antibodies against known marker proteins (FIG. 8C). Blotting each fraction with our anti-PTPMT1 antibody revealed PTPMT1 to be highly enriched only in the IM-containing SMP and MP fractions. This result was nearly indistinguishable from that of the adenine nucleotide translocator (ANT) immunoblot used as a marker for the inner membrane. Together with the EM immunogold staining pattern, these results strongly suggest PTPMT1 to be a mitochondrial inner membrane phosphatase.

PTPMT1 is Anchored to the Matrix Face of the Inner Membrane

Figure 8D:
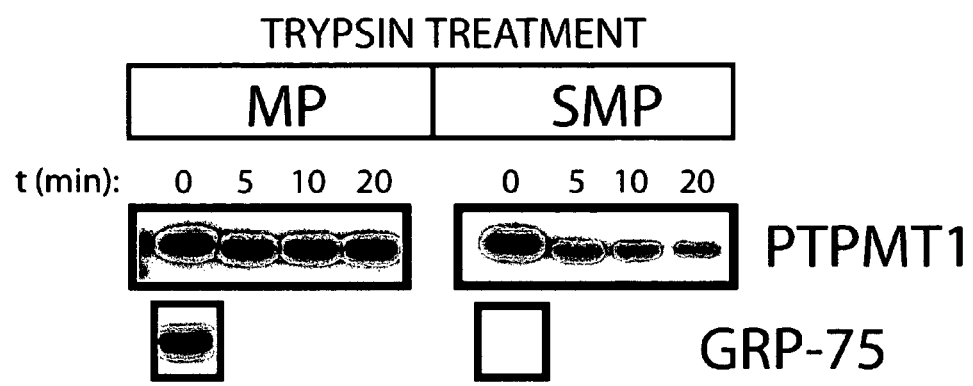
Figure 8E:
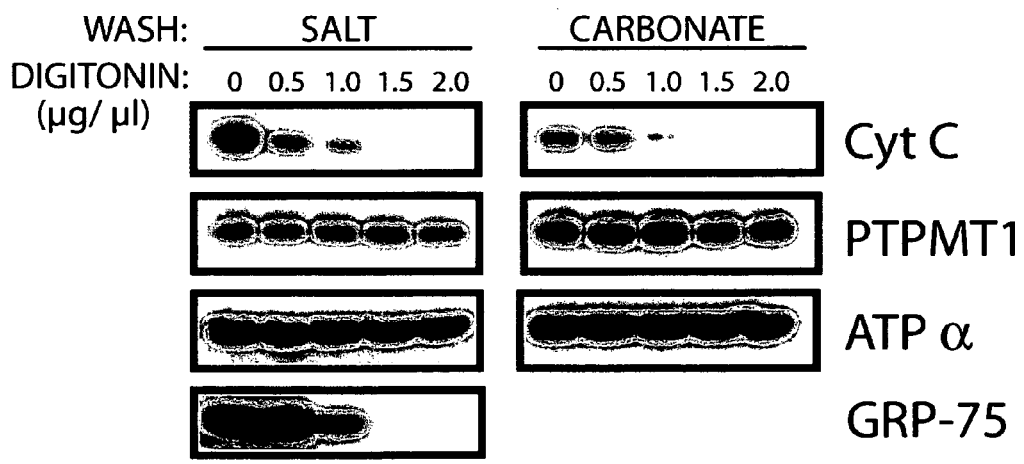

Proteins attached to the inner mitochondrial membrane may face either the matrix or the IMS. As the biochemical responsibilities of these compartments are vastly different, Applicants sought to determine PTPMT1's orientation on this membrane. MPs, which expose the cytosolic face of the IM, and SNPs, which expose the matrix face of the IM, were used as tools to discern PTPMT1's membrane orientation. Both mitochondrial species were treated with trypsin for varying times to digest proteins off each surface. After termination with soybean trypsin inhibitor, samples were pelleted and the soluble trypsinized material removed. Immunoblots of PTPMT1 from the trypsinized pellet fractions revealed a gradual loss of PTPMT1 from SMPs, but no change from MPs, demonstrating PTPMT1 to be present on the matrix (inner) face of the IM (FIG. 8D). Furthermore, PTPMT1's association with the IM was robust; similar to ATP synthase, Applicants were unable to dislodge PTPMT1 with a high salt (200 mM KCl) or pH 11.5 carbonate wash from digitonin-permeabilized mitochondria (FIG. 8E) or SMPs.

Knockdown of PTPMT1 Expression Enhances ATP Production

Figure 9:
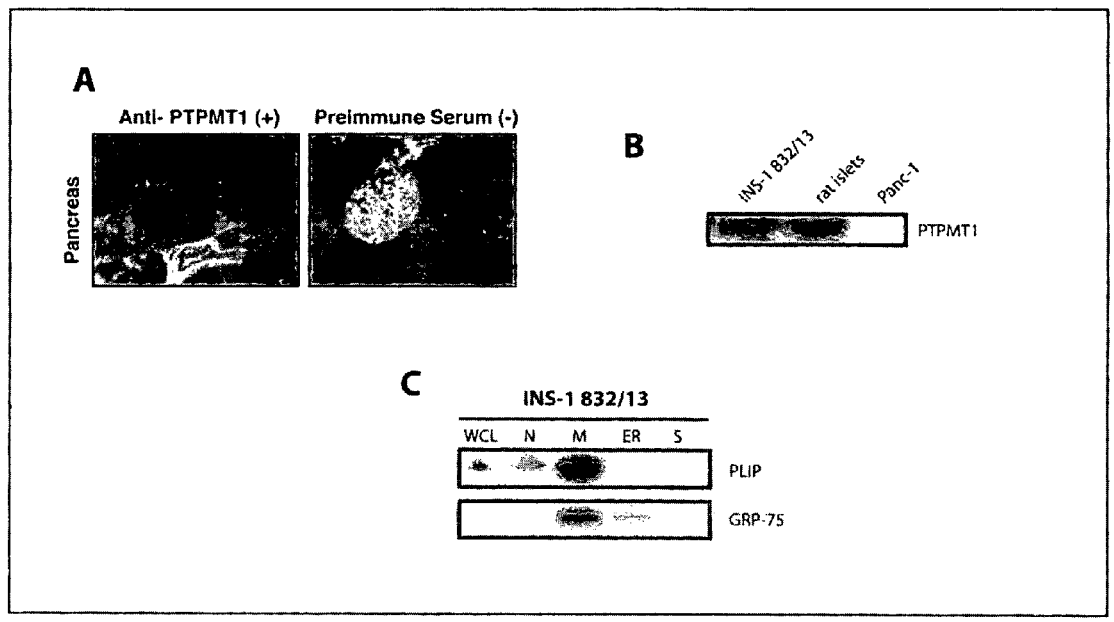
FIG. 9 illustrates that PTPMT1 is present in β cell mitochondria. A is an immunohistochemistry of rat pancreas sections using anti-PTPMT1 or preimmune serum (red=positive staining). In B whole cell lysate form INS-1 832/13 cells, purified rat islets, and Panc-1 cells separated by SDS-PAGE and immunoblotted for PTPMT1. C shows an immunoblot of INS-1 832/13 whole cell lysate, or differential centrifugation fractions with antibodies against either PTPMT1 or mitochondrial marker GRP-75.

FIG. 9 illustrates that PTPMT1 is present in β-cell mitochondria. A is an immunohistochemistry of rat pancreas sections using anti-PTPMT1 or preimmune serum (red=positive staining). In B fifty µg of whole cell lysate from INS-1 832/13 cells, purified rat islets, and Panc-1 cells separated by SDS-PAGE and immunoblotted for PTPMT1 are shown. C shows an immunoblot of INS-1 832/13 whole cell lysate (WCL), or differential centrifugation fractions (N—nucleus/unbroken cells, M—mitochondria, ER—ER-rich post-mitochondrial supernatant, and S—soluble material) with antibodies against either PTPMT1 or mitochondrial marker GRP-75.

An immunohistochemical (IHC) analysis revealed PTPMT1 to be expressed in various mouse tissues including testes, liver, kidney, and the endocrine cells of the pancreas (FIG. 9A). To further probe the specific cell type within the pancreas where PTPMT1 resides, Applicants immunoblotted whole cell lysate from purified rat islets, the glucose responsive insulinoma cell line INS-1 832/13 (Hohmeier et al., 2000), and the exocrine pancreas-derived cell line panc-1. Both the islets and the INS-1 cell line displayed immunoreactive PTPMT1, but, consistent with the IHC results, no staining was seen from the panc-1 cell line (FIG. 9B). To be certain that PTPMT1 from the INS-1 832/13 cell line also localized to the mitochondria, these cells were fractionated by differential centrifugation and immunoblotted for PTPMT1. Consistent with our endogenous PTPMT1 result from rat liver, >90% of PTPMT1 from this cell line was found in the mitochondrial fraction (FIG. 9C).

Figure 10:
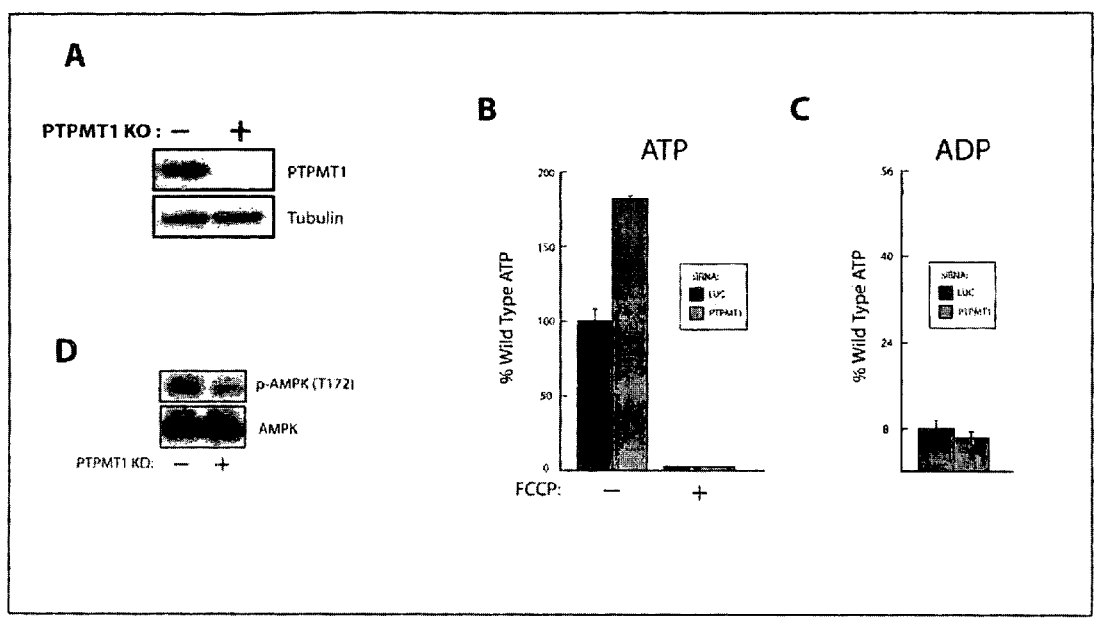
FIG. 10 illustrates that PTPMT1 is involved in the regulation of mitochondrial ATP production. A shows an immunoblot of PTPMT1 or tubulin whole cell lysate from INS-1 832/13 cells treated with siRNA against either luciferase (−) or PTPMT1 (+). In B whole cell ATP content of INS-1 832/13 cells was incubated in low glucose media±FCCP, siRNA treatment. In C whole cell ADP was measured as above. D shows immunoblots of AMPK and phospho-threonine 172 AMPK from control and PTPMT1 knockdown cells treated as above.

FIG. 10 illustrates that PTPMT1 is involved in the regulation of mitochondrial ATP production. A shows an immunoblot of PTPMT1 or tubulin (loading control) from 20 μg of whole cell lysate from INS-1 832/13 cells treated with siRNA against either luciferase (−) or PTPMT1 (+). In B whole cell ATP content of INS-1 832/13 cells was incubated for 2 h in low glucose media±FCCP, as described in the text, 72 hours post siRNA treatment. Error bars indicate standard deviation from three experiments. In C whole cell ADP was measured as above. D shows immunoblots of AMPK and phospho-threonine 172 AMPK from control and PTPMT1 knockdown cells treated as above.

Given PTPMT1's likely juxtaposition with members of the respiratory chain on the inner mitochondrial membrane, assessment of PTPMT1's endogenous function was carried out by measuring its effect on cellular ATP levels. To this end, luciferase control or PTPMT1 siRNA was introduced into the INS-1 832/13 cell line using the Amaxa nucleoporation system, which proved to be highly effective at ablating endogenous PTPMT1 expression (FIG. 10A). Seventy-two hours post siRNA treatment, cells were washed and incubated in a 3.0 mM glucose medium for 2 hr. Cells were then lysed and ATP levels analyzed using a luciferase based luminometry reaction. Strikingly, knockdown of PTPMT1 expression increased ATP levels by an average of 82% over control cells across three separate experiments (FIG. 10B). Cells incubated in the same buffer containing 10 μM FCCP, a mitochondrial uncoupling agent, showed no difference in ATP levels, indicating that the enhanced cellular ATP pool seen in the PTPMT1 knockdown cells is of mitochondrial origin (FIG. 10B). PTPMT1 had extremely poor ATPase activity in vitro, making it highly unlikely that PTPMT1's effect on ATP levels results from direct hydrolysis of this substrate in vivo. Very little, if any, difference was seen in ADP levels between WT and PTPMT1 knockdown cells, indicating there to be a substantial increase in the cellular ATP/ADP ratio (FIG. 10C). To further demonstrate this, the phosphorylation state of AMP-activated protein kinase (AMPK) was analyzed. AMPK serves as a sensor of cellular energy status, becoming dephosphorylated (inactivated) when the cellular AMP:ATP ratio decreases. Consistent with the above data, AMPK is more highly phosphorylated in the control cells following the above incubation in low glucose (FIG. 10D). Thus, knockdown of PTPMT1 results in a true increase in cellular energy status, as opposed to merely a general increase in the cellular adenine pool. Together, these data indicate that PTPMT1 may play a fundamental role in energy homeostasis by serving as a regulator of mitochondrial ATP production.

PTPMT1 is Involved in the Regulation of Insulin Secretion in Pancreatic β Cells

A unique role for the mitochondria of pancreatic β cells is in the coupling of glucose metabolism to insulin secretion (Maechler and Wollheim, 2001). In these cells, pyruvate resulting from glycolysis is efficiently transported into the mitochondria where it is further metabolized into acetyl-CoA by the pyruvate dehydrogenase complex (PDC), eventually leading to an increase in ATP production via oxidative phosphorylation. An increase in the cellular ATP/ADP ratio subsequently serves as an impetus for the insulin secretion response (Straub and Sharp, 2002).

Figure 11:
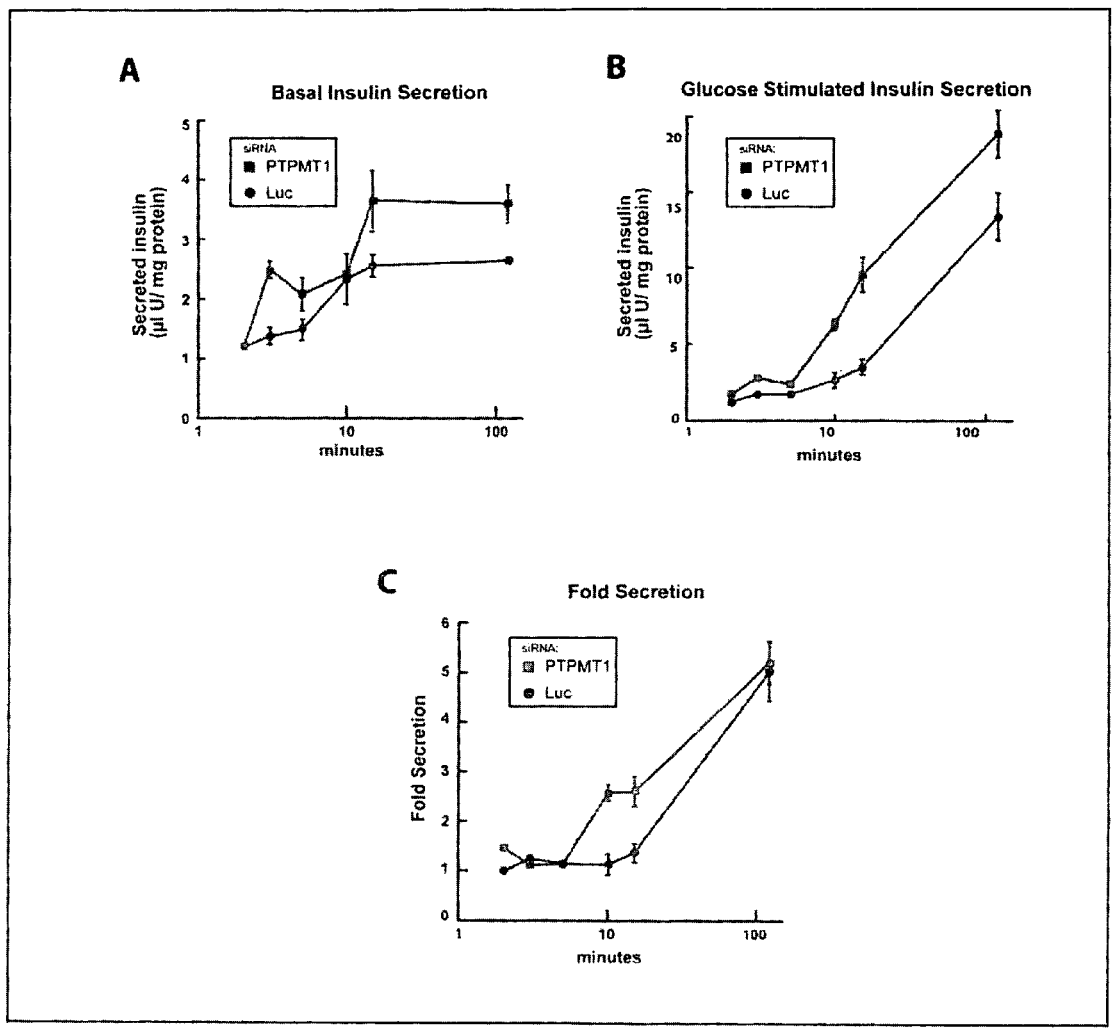
FIG. 11 illustrates that PTPMT1 knockdown cells demonstrate enhanced insulin secretion. In A and B time course of insulin secretion in INS-1 832/13 cells following stimulation with 3 mM (A) or 15 mM glucose media (B) following a 2 hr preincubation in 3 mM glucose media are shown. C shows fold stimulation of insulin secretion for control and PTPMT1 knockdown cells.

FIG. 11 illustrates that PTPMT1 knockdown cells demonstrate enhanced insulin secretion. In A and B time course of insulin secretion in INS-1 832/13 cells following stimulation with 3 mM (A) or 15 mM glucose media (B) following a 2 hr preincubation in 3 mM glucose media are shown. Error bars represent standard deviation of triplicate samples are shown. C shows fold stimulation of insulin secretion (average insulin secreted under high glucose conditions divided by average insulin secreted by low glucose conditions) at each timepoint for control and PTPMT1 knockdown cells.

The finding that ablation of PTPMT1 expression leads to a marked increase in ATP levels prompted us to examine whether inhibiting PTPMT1 function in this manner had a downstream effect on insulin secretion. To test this, INS-1 832/13 cells were again treated with luciferase (control) or PTPMT1 siRNA. Seventy-two hours post siRNA treatment, cells were washed with PBS, and incubated in media containing 3 mM glucose for 2 hrs to normalize insulin release. Fresh media containing either 3 mM (low) or 15 mM (high) glucose media was then added to the cells and insulin secretion analyzed out to 120 min. Both control and PTPMT1 knockdown cells exhibited the expected biphasic response to glucose stimulation (Straub and Sharp, 2002). The PTPMT1 knockdown cells, however, showed increased insulin secretion at nearly all time points under both basal (low) and glucose stimulated (high) conditions (FIGS. 11A,B). PTPMT1 knockdown increased glucose-stimulated insulin secretion (GSIS) at a much greater rate than basal glucose insulin secretion, especially at the beginning of the second, sustained phase (FIG. 11C). This suggests that PTPMT1 has a more significant effect on the insulin secretion response than merely decreasing the threshold for secretion. Together, our observation that knockdown of PTPMT1 expression leads to a strong enhancement of GSIS indicates that the ability of pancreatic β cells to properly release insulin is in part controlled by a phosphorylation event within the mitochondrion.

Disruption of PTPMT1 Expression Affects the Mitochondrial Phosphoprotein Profile of INS-1 832/13 Cells The 107 members of the PTP superfamily are known to utilize a variety of proteinaceous and non-proteinaceous substrates in vitro and in vivo. Included in this group are phosphotyrosine-, phosphothreonine-, and phosphoserine-containing proteins, RNA, and the phosphoinositide (PI) family of lipid signaling molecules. Applicants have previously reported PTPMT1 to possess a highly specific in vitro activity for the rare phosphoinositide PI(5)P, but have yet to demonstrate PTPMT1 to alter the level of this lipid in vivo. Although there is a least one report of a more abundant PI existing within mitochondria (Whipps et al., 1987), there has been no report of PI(5)P existing within this organelle.

Figure 12:
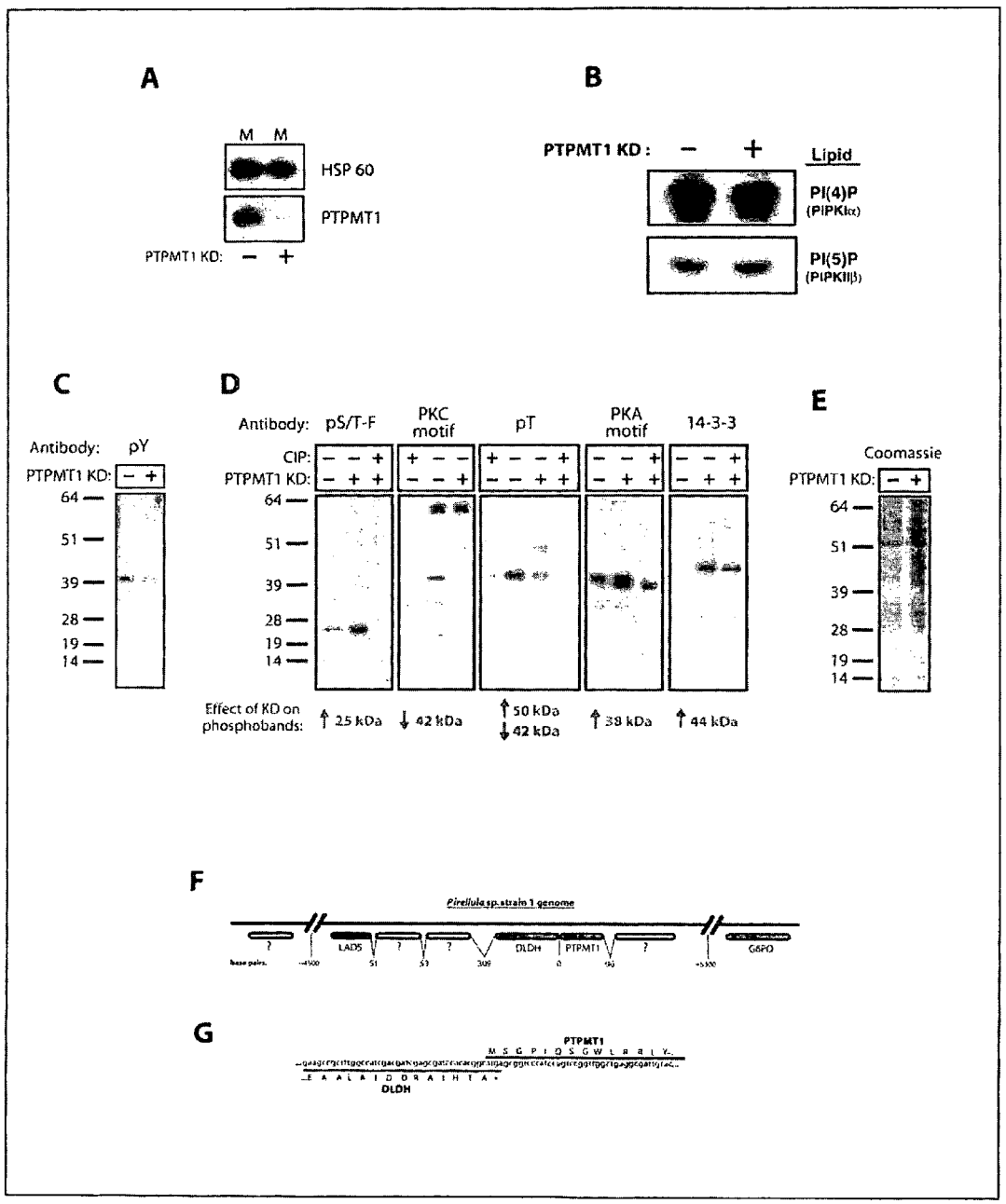
FIG. 12 illustrates that knockdown of PTPMT1 alters the mitochondrial phosphoprotein profile. A shows immunoblots of the mitochondrial marker HSP 60 or PTPMT1 from density gradient purified INS-1 832/13 mitochondria from control and adenovirus-mediated PTPMT1 knockdown cells. B shows PI(4)P and PI(5)P levels from control and PTPMT1 knockdown cells analyzed by TLC followed by autoradiography. C shows mitochondrial protein from control and PTPMT1 knockdown cells immunoblotted for phospho-tyrosine containing proteins using a phospho-tyrosine (pY) specific antibody. In D the same as in C with various phospho-serine or phospho-threonine specific antibodies is shown. B shows Coomassie stained gel of control and PTPMT1 knockdown mitochondria. F is a schematic of a section of *Pirellula* sp. Strain 1 genome. G shows DNA and primary amino acid sequences of the DLDH and PTPMT1 genes (SEQ ID NOs: 41-43).

FIG. 12 shows that knockdown of PTPMT1 alters the mitochondrial phosphoprotein profile. FIG. 12A shows immunoblots of the mitochondrial marker HSP 60 or PTPMT1 from 5 μg of density gradient purified INS-1 832/13 mitochondria from control and adenovirus-mediated PTPMT1 knockdown cells. B shows PI(4)P and PI(5)P levels from control and PTPMT1 knockdown cells analyzed by TLC followed by autoradiography. In C ten μg of mitochondrial protein from control and PTPMT1 knockdown cells were immunoblotted for phospho-tyrosine containing proteins using a phospho-tyrosine (pY) specific antibody. In D the same as in C in shown, with various phospho-serine or phospho-threonine specific antibodies (e.g., "pS/T-F" indicates an antibody raised against peptides possessing a motif of a phospho-serine or -threonine followed by a phenylalanine, "PKC motif" indicates an antibody raised against the phosphorylated recognition motif of protein kinase C, etc. See the Cell Signaling Technology catalog 2005 for further information.) Samples were treated±calf intestinal phosphatase (CIP) before blotting as indicated. Effects of PTPMT1 knockdown on various phosphoproteins is indicated below each blot (green "up" arrow indicates an increase in the phosphorylation state, red "down" arrow indicates a decrease in phosphorylation). E shows Coomassie stained gel of 10 µg of control and PTPMT1 knockdown mitochondria. F is a schematic of a section of *Pirellula* sp. Strain 1 genome. Genes are represented as ovals with the intervening base pairs listed below. LADS—Lipid A Disaccharide Synthase; DLDH—Dihydrolipoamide Dehydrogenase; G6PD—Glucose 6-Phosphate Dehydrogenase; ?—Unknown or uncharacterized gene. Adapted from Glockner, F. O., et. al. G shows DNA and primary amino acid sequences of the DLDH and PTPMT1 genes. Overlapping DNA sequence is shown in blue.

To simultaneously assess the effect that knockdown of PTPMT1 has on mitochondrial phosphoproteins and PI(5)P levels, its expression was knocked-down in a large quantity of INS-1 832/13 cells using adenovirus-delivered siRNA. Similar to the Amaxa treatment, this technique was highly effective at ablating PTPMT1 expression (FIG. 12A). Seventy-two hours post-infection, all cells were treated with low glucose buffer for 2 h, as described above. Cells were then harvested and the mitochondria purified via differential and density-gradient centrifugation as described above. To assess the effect of PTPMT1 expression on mitochondrial PI(5)P, total mitochondrial lipids were extracted by the Bligh-Dyer method. The levels of PI(5)P and PI(4)P (control) were then measured by their conversion to $PI(4,5)P_2$ by PIPKIIβ (a PI(5)P-4kinase) and PIPKIα (a PI(4)P-5kinase), respectively, in an in vitro reaction (Clarke et al., 2001). A TLC of the reaction products revealed PI(4)P to be present at relatively high levels, whereas PI(5)P was barely detectable. No significant difference was observed in either of these lipids between the control and PTPMT1 knockdown samples, suggesting PI(5)P to be an unlikely endogenous substrate of PTPMT1 (FIG. 12B).

To assess the effect of the PTPMT1 KD on mitochondrial phosphoprotein levels, 10 µg of mitochondrial protein from control and PTPMT1 knockdown cells were separated by SDS-PAGE and immunoblotted with various phospho-specific antibodies. No difference was seen using a phosphotyrosine (pY) antibody (FIG. 12C), but prominent differences were observed with antibodies against various phospho-threonine or phospho-threonine/serine motifs (FIG. 12D). Each of these bands were diminished or eliminated when the samples were treated with calf intestinal phosphatase (CIP) prior to performing the immunoblots, indicating these bands to be bona fide phosphoproteins (FIG. 12D). A coomassie stain of an identical amount of sample was performed to ensure equal loading (FIG. 12E). Four of these proteins became more highly phosphorylated following the PTPMT1 knockdown, consistent with them serving as possible in vivo substrates. Two other bands (possibly representing the same protein) are more phosphorylated in the control mitochondria, suggesting an indirect or downstream effect resulting from the PTPMT1 knockdown. Furthermore, although multiple antibodies were used primarily to increase the likelihood of detecting a given phosphoprotein, Applicants note that PKC, PKA, and 14-3-3 have all been reported to exist within mitochondria (Bunney et al., 2001; Horbinski and Chu, 2005). Together, despite PTPMT1's in vitro activity, this analysis favors a hypothesis that PTPMT1 acts as a protein phosphatase in vivo.

Discussion

Our analysis of PTPMT1, the newest member of this family, extends the reach of PTPs into a new and important venue: the mitochondrion. The establishment of PTPMT1 as a resident member of this organelle, coupled with the recent discovery of a handful of mitochondrial kinases (Horbinski and Chu, 2005; Valente et al., 2004), bolsters the claim that the mitochondrion is an underappreciated site of signaling by phosphorylation.

Applicants have demonstrated that PTPMT1 is one of the most highly conserved PTPs known (Pagliarini et al., 2004). Here, Applicants show that PTPMT1 appears to be involved in the regulation of one of the cell's most fundamental metabolic parameters: cellular ATP content. In rat INS-1 832/13 cells, knockdown of PTPMT1 expression leads to a substantial increases in cellular ATP levels, which are known to have a direct effect on the rate of insulin secretion. It is not surprising, therefore, that loss of PTPMT1 in these cells enhances this process under both basal and glucose stimulated conditions. Furthermore, the effect of PTPMT1 knockdown is seen in both phases of insulin secretion, especially at the beginning of the second, sustained phase. Whereas ATP levels are known to direct the first phase of insulin secretion, its role in the second phase remains nebulous (Straub and Sharp, 2002). Our results here either suggest that ATP levels have a more global affect on the insulin secretion response, or that the PTPMT1 has a more far-reaching effect on β cells than ATP production alone. Nonetheless, enhancement of insulin secretion, most often through the use of sulfonylureas, is the most common means of treating type II diabetes (Proks et al., 2002). Thus, PTPMT1 has the potential of becoming an effective therapeutic target for this disease.

The direct substrate(s) for PTPMT1 that mediates our observed biological effects remain elusive. Despite the robust in vitro activity PTPMT1 possesses for the phosphoinositide PI(5)P, there is currently no evidence of this phosphoinositide residing in the mitochondrion, and we have yet to observe any changes in PI(5)P levels in vivo upon knockdown of PTPMT1 expression. In INS-1 832/13 cells, however, this knockdown results in a change in the mitochondrial phosphoprotein profile, suggesting that PTPMT1 may actually act as a protein phosphatase within the mitochondrion. Other circumstantial evidence suggests the same. PTPMT1's position on the inner mitochondrial membrane places it near pathways that can directly impact ATP levels: oxidative phosphorylation (OXPHOS) and the TCA cycle, both of which include reported phosphoproteins. In the genome of the eubacterium *Pirellula*, the only organism to date with a PTPMT1 ortholog that lacks mitochondria, the PTPMT1 start codon overlaps with the stop codon for dihydrolipoamide dehydrogenase, the E3 subunit of the pyruvate and branched-chain α-ketoacid dehydrogenase complexes, in what seems likely to be a bacterial operon (FIGS. 12 F,G) (Glockner et al., 2003). Thus, it seems reasonable to speculate that PTPMT1 is involved in the regulation of ATP production within the PDC-TCA-OXPHOS pathway. Further analysis of PTPMT1's endogenous substrate, and the development of knockout mouse models, are ongoing.

REFERENCES

1. Tonks, N. K., and Neel, B. G. (2001) *Curr Opin Cell Biol* 13, 182-195
2. Li, L., and Dixon, J. E. (2000) *Semin Immunol* 12, 75-84
3. Andersen, J. N., Mortensen, O. H., Peters, G. H., Drake, P. G., Iversen, L. F., Olsen, O. H., Jansen, P. G., Andersen, H. S., Tonks, N. K., and Moller, N. P. (2001) *Mol Cell Biol* 21, 7117-7136
4. Fauman, E. B., and Saper, M. A. (1996) *Trends Biochem Sci* 21, 413-417
5. Jackson, M. D., and Denu, J. M. (2001) *Chem Rev* 101, 2313-2340

6. Lee, J. O., Yang, H., Georgescu, M. M., Di Cristofano, A., Maehama, T., Shi, Y., Dixon, J. E., Pandolfi, P., and Pavletich, N. P. (1999) *Cell* 99, 323-334
7. Morris, J. B., Hinchliffe, K. A., Ciruela, A., Letcher, A. J., and Irvine, R. F. (2000) *FEBS Lett* 475, 57-60
8. Walker, S. M., Downes, C. P., and Leslie, N. R. (2001) *Biochem J* 360, 277-283
9. Wu, Y., Dowbenko, D., Pisabarro, M. T., Dillard-Telm, L., Koeppen, H., and Lasky, L. A. (2001) *J Biol Chem* 276, 21745-21753
10. Niebuhr, K., Giuriato, S., Pedron, T., Philpott, D. J., Gaits, F., Sable, J., Sheetz, M. P., Parsot, C., Sansonetti, P. J., and Payrastre, B. (2002) *Embo J* 21, 5069-5078
11. Norris, F. A., Wilson, M. P., Wallis, T. S., Galyov, E. E., and Majerus, P. W. (1998) *Proc Natl Acad Sci USA* 95, 14057-14059
12. Bansal, V. S., Caldwell, K. K., and Majerus, P. W. (1990) *J Biol Chem* 265, 1806-1811
13. Norris, F. A., and Majerus, P. W. (1994) *J Biol Chem* 269, 8716-8720
14. Vanhaesebroeck, B., Leevers, S. J., Ahmadi, K., Timms, J., Katso, R., Driscoll, P. C., Woscholski, R., Parker, P. J., and Waterfield, M. D. (2001) *Annu Rev Biochem* 70, 535-602
15. Wishart, M. J., and Dixon, J. E. (2002) *Trends Cell Biol* 12, 579-585
16. Rameh, L. E., Tolias, K. F., Duckworth, B. C., and Cantley, L. C. (1997) *Nature* 390, 192-196
17. Clarke, J. H., Letcher, A. J., D'Santos C, S., Halstead, J. R., Irvine, R. F., and Divecha, N. (2001) *Biochem J* 357, 905-910
18. Meijer, H. J., Berrie, C. P., Iurisci, C., Divecha, N., Musgrave, A., and Munnik, T. (2001) *Biochem J* 360, 491-498
19. Gozani, O., Karuman, P., Jones, D. R., Ivanov, D., Cha, J., Lugovskoy, A. A., Baird, C. L., Zhu, H., Field, S. J., Lessnick, S. L., Villasenor, J., Mehrotra, B., Chen, J., Rao, V. R., Brugge, J. S., Ferguson, C. G., Payrastre, B., Myszka, D. G., Cantley, L. C., Wagner, G., Divecha, N., Prestwich, G. D., and Yuan, J. (2003) *Cell* 114, 99-111
20. Carricaburu, V., Lamia, K. A., Lo, E., Favereaux, L., Payrastre, B., Cantley, L. C., and Rameh, L. E. (2003) *Proc Natl Acad Sci USA* 100, 9867-9872
21. Schaletzky, J., Dove, S. K., Short, B., Lorenzo, O., Clague, M. J., and Barr, F. A. (2003) *Curr Biol* 13, 504-509
22. Taylor, G. S., and Dixon, J. E. (2003) *Methods Enzymol* 366, 43-56
23. Taylor, G. S., Liu, Y., Baskerville, C., and Charbonneau, H. (1997) *J Biol Chem* 272, 24054-24063
24. Worby, C. A., Simonson-Leff, N., and Dixon, J. E. (2001) *Sci STKE* 2001, PL1
25. Clemens, J. C., Worby, C. A., Simonson-Leff, N., Muda, M., Maehama, T., Hemmings, B. A., and Dixon, J. E. (2000) *Proc Natl Acad Sci USA* 97, 6499-6503
26. Altschul, S. F., Gish, W., Miller, W., Myers, E. W., and Lipman, D. J. (1990) *J Mol Biol* 215, 403-410
27. Altschul, S. F., Madden, T. L., Schaffer, A. A., Zhang, J., Zhang, Z., Miller, W., and Lipman, D. J. (1997) *Nucleic Acids Res* 25, 3389-3402
28. Lindsay, M. R., Webb, R. I., Strous, M., Jetten, M. S., Butler, M. K., Forde, R. J., and Fuerst, J. A. (2001) *Arch Microbiol* 175, 413-429
29. Glockner, F. O., Kube, M., Bauer, M., Teeling, H., Lombardot, T., Ludwig, W., Gade, D., Beck, A., Borzym, K., Heitmann, K., Rabus, R., Schlesner, H., Amann, R., and Reinhardt, R. (2003) *Proc Natl Acad Sci USA* 100, 8298-8303
30. Merlot, S., Meili, R., Pagliarini, D. J., Maehama, T., Dixon, J. E., and Firtel, R. A. (2003) *J Biol Chem*
31. Mochizuki, Y., and Majerus, P. W. (2003) *Proc Natl Acad Sci USA* 100, 9768-9773
32. Taylor, G. S., Maehana, T., and Dixon, J. E. (2000) *Proc Natl Acad Sci USA* 97, 8910-8915
33. Ishibashi, T., Bottaro, D. P., Chan, A., Miki, T., and Aaronson, S. A. (1992) *Proc Natl Acad Sci USA* 89, 12170-12174
34. Zhao, Z., Zander, N. F., Malencik, D. A., Anderson, S. R., and Fischer, E. H. (1992) *Anal Biochem* 202, 361-366
35. Ruzzene, M., Donella-Deana, A., Marin, O., Perich, J. W., Ruzza, P., Borin, G., Calderan, A., and Pinna, L. A. (1993) *Eur J Biochem* 211, 289-295
36. Zhou, G., Denu, J. M., Wu, L., and Dixon, J. E. (1994) *J Biol Chem* 269, 28084-28090
37. Denu, J. M., Zhou, G., Wu, L., Zhao, R., Yuvaniyama, J., Saper, M. A., and Dixon, J. E. (1995) *J Biol Chem* 270, 3796-3803
38. Terebiznik, M. R., Vieira, O. V., Marcus, S. L., Slade, A., Yip, C. M., Trimble, W. S., Meyer, T., Finlay, B. B., and Grinstein, S. (2002) *Nat Cell Biol* 4, 766-773
39. Maehama, T., and Dixon, J. E. (1998) *J Biol Chem* 273, 13375-13378
40. Tronchere, H., Laporte, J., Pendaries, C., Chaussade, C., Liaubet, L., Pirola, L., Mandel, J. L., and Payrastre, B. (2003) *J Biol Chem*
41. Weinkove, D., Leevers, S. J., MacDougall, L. K., and Waterfield, M. D. (1997) *J Biol Chem* 272, 14606-14610
42. Lizcano, J. M., Alrubaie, S., Kieloch, A., Deak, M., Leevers, S. J., and Alessi, D. R. (2003) *Biochem J* 374, 297-306
43. Alonso, A., Sasin, J., Bottini, N., Friedberg, I., Osterman, A., Godzik, A., Hunter, T., Dixon, J., and Mustelin, T. (2004). Protein tyrosine phosphatases in the human genome. Cell 117, 699-711.
44. Andersen, J. N., Jansen, P. G., Echwald, S. M., Mortensen, O. H., Fukada, T., Del Vecchio, R., Tonks, N. K., and Moller, N. P. (2004). A genomic perspective on protein tyrosine phosphatases: gene structure, pseudogenes, and genetic disease linkage. Faseb J 18, 8-30.
45. Bijur, G. N., and Jope, R. S. (2003). Rapid accumulation of Akt in mitochondria following phosphatidylinositol 3-kinase activation. J Neurochem 87, 1427-1435.
46. Bunney, T. D., van Walraven, H. S., and de Boer, A. H. (2001). 14-3-3 protein is a regulator of the mitochondrial and chloroplast ATP synthase. Proc Natl Acad Sci USA 98, 4249-4254.
47. Bykova, N. V., Egsgaard, H., and Moller, I. M. (2003). Identification of 14 new phosphoproteins involved in important plant mitochondrial processes. FEBS Lett 540, 141-146.
48. Chen, R., Fearnley, I. M., Peak-Chew, S. Y., and Walker, J. E. (2004). The phosphorylation of subunits of complex I from bovine heart mitochondria. J Biol Chem 279, 26036-26045.
49. Clarke, J. H., Letcher, A. J., D'Santos C, S., Halstead, J. R., Irvine, R. F., and Divecha, N. (2001). Inositol lipids are regulated during cell cycle progression in the nuclei of murine erythroleukaemia cells. Biochem J 357, 905-910.
50. Felgner, P. L., Messer, J. L., and Wilson, J. E. (1979). Purification of a hexokinase-binding protein from the outer mitochondrial membrane. J Biol Chem 254, 4946-4949.
51. Glockner, F. O., Kube, M., Bauer, M., Teeling, H., Lombardot, T., Ludwig, W., Gade, D., Beck, A., Borzym, K., Heitmann, K., et al. (2003). Complete genome sequence of the marine planctomycete *Pirellula* sp. strain 1. Proc Natl Acad Sci. USA 100, 8298-8303.

52. Gorman, M. W., Marble, D. R., Ogimoto, K., and Feigl, E. O. (2003). Measurement of adenine nucleotides in plasma. Luminescence 18, 173-181.
53. Harlow, E., and Lane, D. (1988). Antibodies: A Lab Manual, Cold Spring Harbor Labs).
54. Harris, R. A., Hawes, J. W., Popov, K. M., Zhao, Y., Shimomura, Y., Sato, J., Jaskiewicz, J., and Hurley, T. D. (1997). Studies on the regulation of the mitochondrial alpha-ketoacid dehydrogenase complexes and their kinases. Adv Enzyme Regul 37, 271-293.
55. Hogan, B., Beddington, F., Constantini, F., and Lacy, E. (1994). Manipulating the Mouse Embryo: A Laboratory Manual (Woodbury, N.Y., Cold Spring Harbor Lab. Press).
56. Hohmeier, H. E., Mulder, H., Chen, G., Henkel-Rieger, R., Prentki, M., and Newgard, C. B. (2000). Isolation of INS-1-derived cell lines with robust ATP-sensitive K+ channel-dependent and -independent glucose-stimulated insulin secretion. Diabetes 49, 424-430.
57. Hojlund, K., Wrzesinski, K., Larsen, P. M., Fey, S. J., Roepstorff, P., Handberg, A., Dela, F., Vinten, J., McCormack, J. G., Reynet, C., and Beck-Nielsen, H. (2003). Proteome analysis reveals phosphorylation of ATP synthase beta-subunit in human skeletal muscle and proteins with potential roles in type 2 diabetes. J Biol Chem 278, 10436-10442.
58. Horbinski, C., and Chu, C. T. (2005). Kinase signaling cascades in the mitochondrion: a matter of life or death. Free Radic Biol Med 38, 2-11.
59. Lapidus, R. G., and Sokolove, P. M. (1993). Spermine inhibition of the permeability transition of isolated rat liver mitochondria: an investigation of mechanism. Arch Biochem Biophys 306, 246-253.
60. Lee, I., Salomon, A. R., Ficarro, S., Mathes, I., Lottspeich, F., Grossman, L. I., and Huttemann, M. (2004). cAMP-dependent tyrosine phosphorylation of subunit I inhibits cytochrome c oxidase activity. J Biol. Chem.
61. Lesnefsky, E. J., Gudz, T. I., Migita, C. T., Ikeda-Saito, M., Hassan, M. O., Turkaly, P. J., and Hoppel, C. L. (2001). Ischemic injury to mitochondrial electron transport in the aging heart: damage to the iron-sulfur protein subunit of electron transport complex III. Arch Biochem Biophys 385, 117-128.
62. Liou, W., Geuze, H. J., and Slot, J. W. (1996). Improving structural integrity of cryosections for immunogold labeling. Histochem Cell Biol 106, 41-58.
63. Maechler, P., and Wollheim, C. B. (2001). Mitochondrial function in normal and diabetic beta-cells. Nature 414, 807-812.
64. Morris, J. B., Hinchliffe, K. A., Ciruela, A., Letcher, A. J., and Irvine, R. F. (2000). Thrombin stimulation of platelets causes an increase in phosphatidylinositol 5-phosphate revealed by mass assay. FEBS Lett 475, 57-60.
65. Newmeyer, D. D., and Ferguson-Miller, S. (2003). Mitochondria: releasing power for life and unleashing the machineries of death. Cell 112, 481-490.
66. Pagliarini, D. J., Worby, C. A., and Dixon, J. E. (2004). A PTEN-like phosphatase with a novel substrate specificity. J Biol Chem 279, 38590-38596.
67. Pestronka, A. (2004). Mitochondrial Disorders.
68. Proks, P., Reimann, F., Green, N., Gribble, F., and Ashcroft, F. (2002). Sulfonylurea stimulation of insulin secretion. Diabetes 51 Suppl 3, S368-376.
69. Rehling, P., Brandner, K., and Pfanner, N. (2004). Mitochondrial import and the twin-pore translocase. In Nat Rev Mol Cell Biol, pp. 519-530.
70. Roche, T. E., Baker, J. C., Yan, X., Hiromasa, Y., Gong, X., Peng, T., Dong, J., Turkan, A., and Kasten, S. A. (2001). Distinct regulatory properties of pyruvate dehydrogenase kinase and phosphatase isoforms. Prog Nucleic Acid Res Mol Biol 70, 33-75.
71. Salvi, M., Stringaro, A., Brunati, A. M., Agostinelli, E., Arancia, G., Clari, G., and Toninello, A. (2004). Tyrosine phosphatase activity in mitochondria: presence of Shp-2 phosphatase in mitochondria. Cell Mol Life Sci 61, 2393-2404.
72. Schon, E. A. (2000). Mitochondrial genetics and disease. Trends Biochem Sci 25, 555-560.
73. Schulenberg, B., Aggeler, R., Beechem, J. M., Capaldi, R. A., and Patton, W. F. (2003). Analysis of steady-state protein phosphorylation in mitochondria using a novel fluorescent phosphosensor dye. J Biol Chem 278, 27251-27255.
74. Sottocasa, G. L., Kuylenstierna, B., Ernster, L., and Bergstrand, A. (1967). An electron-transport system associated with the outer membrane of liver mitochondria. A biochemical and morphological study. J Cell Biol 32, 415-438.
75. Straub, S. G., and Sharp, G. W. (2002). Glucose-stimulated signaling pathways in biphasic insulin secretion. Diabetes Metab Res Rev 18, 451-463.
76. Tokuyasu, K. T. (1980). Immunochemistry on ultrathin frozen sections. Histochem J 12, 381-403.
77. United Mitochondrial Disease Foundation (2004)
78. Valente, E. M., Abou-Sleiman, P. M., Caputo, V., Muqit, M. M., Harvey, K., Gispert, S., Ali, Z., Del Turco, D., Bentivoglio, A. R., Healy, D. G., et al. (2004). Hereditary early-onset Parkinson's disease caused by mutations in PINK1. Science 304, 1158-1160.
79. Voet, D. a. V., J. G. (2004). Biochemistry, 3rd edn, John Wiley & Sons, Inc.). Wallace, D. C. (1999). Mitochondrial diseases in man and mouse. Science 283, 1482-1488.
80. Whipps, D. E., Armston, A. E., Pryor, H. J., and Halestrap, A. P. (1987). Effects of glucagon and Ca2+ on the metabolism of phosphatidylinositol 4-phosphate and phosphatidylinositol 4,5-bisphosphate in isolated rat hepatocytes and plasma membranes. Biochem J 241, 835-845.

What is claimed is:

1. A method for increasing insulin production by PTPMT1 positive cells comprising contacting PTPMT1-positive cells with a siRNA molecule that recognizes and binds PTPMT1 thereby regulating insulin production.

2. A method for inhibiting the expression of the PTPMT1 gene comprising contacting PTPMT1-positive cells with a siRNA molecule that recognizes and binds PTPMT1 thereby inhibiting the expression of the PTPMT1 gene.

3. A method for treating type II diabetes by inhibiting the expression of the PTPMT1 gene by the method of claim 1.

4. The method of claims 1 or 2, wherein the siRNA molecule comprises a sequence that is GUCUGUGGAUGACAAAGAAtt (SEQ ID NO:3) or UUCUUUGUCAUCCACAGACtt (SEQ ID NO:4) of FIG. 13.

5. The method of claims 1 or 2, wherein the siRNA molecule comprises a sequence that is gccaguuggaaauucucaatt (SEQ ID NO:5) or uugagaauuuccaacuggctg (SEQ ID NO:6) of FIG. 14.

6. The method of claims 1 or 2, wherein the siRNA molecule comprises a sequence that is guuggaaauucucaaagagtt (SEQ ID NO:7) or cucuuugagaauuuccaactg (SEQ ID NO:8) of FIG. 15.

* * * * *